United States Patent
Olson et al.

(10) Patent No.: US 6,300,496 B1
(45) Date of Patent: Oct. 9, 2001

(54) PROCESSES FOR PRODUCING EPSILON CAPROLACTAMS

(75) Inventors: Kurt Damar Olson; Thomas Carl Eisenschmid, both of Cross Lanes; David Robert Bryant, South Charleston; Arthur Roy Doumaux, Jr., Charleston, all of WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 09/413,572

(22) Filed: Oct. 6, 1999

(51) Int. Cl.⁷ ........................ C07D 201/08; C07D 223/10
(52) U.S. Cl. ........................................................ 540/538
(58) Field of Search ............................................. 540/538

(56) References Cited

U.S. PATENT DOCUMENTS

| | | | |
|---|---|---|---|
| 2,840,554 | 6/1958 | Pieper | 260/239.3 |
| 3,000,879 | * 9/1961 | Phillips et al. | 260/239.3 |
| 3,317,516 | 5/1967 | Mifune et al. | 260/239.3 |
| 3,317,517 | 5/1967 | Mifune et al. | 260/239.3 |
| 3,320,241 | 5/1967 | Kyle et al. | 260/239.3 |
| 3,338,889 | 8/1967 | Pesson | 260/239.2 |
| 3,346,567 | 10/1967 | Westerveld et al. | 260/239.3 |
| 3,401,161 | 9/1968 | Westerveld et al. | 260/239.3 |
| 3,655,747 | 4/1972 | Sennewald et al. | 260/530 R |
| 4,285,875 | 8/1981 | Cornils et al. | 260/413 |
| 4,289,708 | 9/1981 | Scott et al. | 260/413 |
| 4,353,832 | 10/1982 | Lecloux | 549/272 |
| 4,485,046 | 11/1984 | Fruchey | 260/413 |
| 4,485,047 | 11/1984 | Fruchey et al. | 260/413 |
| 4,487,720 | 12/1984 | Fruchey | 260/419 |
| 4,529,550 | 7/1985 | Fruchey et al. | 260/413 |
| 4,549,025 | 10/1985 | Dalcanale et al. | 546/327 |
| 4,800,227 | 1/1989 | Matson | 548/543 |
| 4,873,326 | 10/1989 | Jakob et al. | 540/538 |
| 5,068,408 | 11/1991 | Raynor et al. | 562/419 |
| 5,663,388 | 9/1997 | Vargas et al. | 554/132 |
| 5,686,638 | 11/1997 | Kos et al. | 554/134 |
| 5,817,883 | * 10/1998 | Briggs et al. | 568/454 |
| 5,925,754 | * 7/1999 | Maher et al. | 540/485 |
| 5,962,680 | * 10/1999 | Eisenschmid et al. | 540/538 |

* cited by examiner

*Primary Examiner*—Bruck Kifle
(74) *Attorney, Agent, or Firm*—Warren K. Volles

(57) ABSTRACT

This invention relates in part to processes for producing one or more substituted or unsubstituted epsilon caprolactams, e.g., epsilon caprolactam, which comprise (a) converting one or more substituted or unsubstituted hydroxyaldehydes, e.g., 6-hydroxyhexanal, optionally in the presence of a catalyst or a catalyst and promoter, to one or more substituted or unsubstituted hydroxyamides, e.g. 6-hydroxycaproamide, and/or one or more substituted or unsubstituted epsilon caprolactam precursors, e.g., 6-aminocaproamide, epsilon caprolactone, epsilon caprolactone oligomers and esters of 6-hydroxycaproic acid and mixtures thereof, and (b) converting said one or more substituted or unsubstituted hydroxyamides and/or said one or more substituted or unsubstituted epsilon caprolactam precursors, optionally in the presence of a catalyst or a catalyst and promoter, to said one or more substituted or unsubstituted epsilon caprolactams; wherein the amount of byproducts resulting from reduction and/or reductive amination of said one or more substituted or unsubstituted hydroxyaldehydes, e.g., 1,6-hexanediol, aminohexanol, and the like, is no greater than about 10 weight percent, preferably no greater than about 5 weight percent, and more preferably no greater than about 1 weight percent, of the total of said one or more substituted or unsubstituted hydroxyamides and/or one or more substituted or unsubstituted epsilon caprolactam precursors. This invention also relates in part to reaction mixtures containing one or more substituted or unsubstituted epsilon caprolactams as principal product(s) of reaction.

19 Claims, No Drawings

US 6,300,496 B1

PROCESSES FOR PRODUCING EPSILON CAPROLACTAMS

BRIEF SUMMARY OF THE INVENTION

1. Technical Field

This invention relates in part to processes for producing one or more substituted or unsubstituted epsilon caprolactams. This invention also relates in part to reaction mixtures containing one or more substituted or unsubstituted epsilon caprolactams as the desired product(s) of reaction.

2. Background of the Invention

Epsilon caprolactam is a valuable intermediate which is useful, for example, in the production of nylon 6. The processes currently used to produce epsilon caprolactam have various disadvantages. For example, certain processes to epsilon caprolactam generate large amounts of byproducts, e.g., ammonium sulfate. Accordingly, it would be desirable to produce epsilon caprolactam from relatively inexpensive starting materials (e.g., hydroxyaldehydes) and by a process which does not generate undesirable byproducts such as those resulting from reduction and/or reductive amination of hydroxyaldehydes, e.g., diols, ethers, diamines, aminoalcohols and the like. Byproducts such as those resulting from reduction and/or reductive amination of hydroxyaldehydes reduce epsilon caprolactam yield and, in addition, can co-oligomerize, co-polymerize or otherwise react with epsilon caprolactam, further reducing reaction yield. Such byproducts are known to form under reducing conditions as well as under non-reducing conditions in reactions such as the Cannizzaro reaction and the Tishchenko reaction.

DISCLOSURE OF THE INVENTION

This invention relates in part to processes for producing one or more substituted or unsubstituted epsilon caprolactams, e.g., epsilon caprolactam, which comprise (a) converting one or more substituted or unsubstituted hydroxyaldehydes, e.g., 6-hydroxyhexanal, optionally in the presence of a catalyst or a catalyst and promoter, to one or more substituted or unsubstituted hydroxyamides, e.g. 6-hydroxycaproamide, and/or one or more substituted or unsubstituted epsilon caprolactam precursors, e.g., 6-aminocaproamide, epsilon caprolactone, epsilon caprolactone oligomers and esters of 6-hydroxycaproic acid and mixtures thereof, and (b) converting one or more substituted or unsubstituted hydroxyamides and/or said one or more substituted or unsubstituted epsilon caprolactam precursors, optionally in the presence of a catalyst or a catalyst and promoter, to said one or more substituted or unsubstituted epsilon caprolactams; wherein the amount of byproducts resulting from reduction and/or reductive amination of said one or more substituted or unsubstituted hydroxyaldehydes, e.g., 1,6-hexanediol, aminohexanol, and the like, is no greater than about 10 weight percent, preferably no greater than about 5 weight percent, and more preferably no greater than about 1 weight percent, of the total of said one or more substituted or unsubstituted hydroxyamides and/or one or more substituted or unsubstituted epsilon caprolactam precursors. Such processes may be conducted in one or more steps or stages.

This invention also relates in part to processes for producing one or more substituted or unsubstituted epsilon caprolactams, e.g., epsilon caprolactam, which comprise (a) converting one or more substituted or unsubstituted hydroxyaldehydes, e.g., 6-hydroxyhexanal, optionally in the presence of a catalyst or a catalyst and promoter, to one or more substituted or unsubstituted hydroxyacids, e.g. 6-hydroxycaproic acid, and/or one or more substituted or unsubstituted epsilon caprolactam precursors, e.g., epsilon caprolactone, epsilon caprolactone oligomers and esters of 6-hydroxycaproic acid and mixtures thereof, and (b) converting said one or more substituted or unsubstituted hydroxyacids and/or said one or more substituted or unsubstituted epsilon caprolactam precursors, optionally in the presence of a catalyst or a catalyst and promoter, to said one or more substituted or unsubstituted epsilon caprolactams; wherein the amount of byproducts resulting from reduction and/or reductive amination of said one or more substituted or unsubstituted hydroxyaldehydes, e.g., 1,6-hexanediol, aminohexanol, and the like, is no greater than about 10 weight percent, preferably no greater than about 5 weight percent, and more preferably no greater than about 1 weight percent, of the total of said one or more substituted or unsubstituted hydroxyacids and/or one or more substituted or unsubstituted epsilon caprolactam precursors. Such processes may be conducted in one or more steps or stages.

This invention further relates in part to processes for producing one or more substituted or unsubstituted epsilon caprolactams, e.g., epsilon caprolactam, which comprise (a) subjecting one or more substituted or unsubstituted hydroxyaldehydes, e.g., 6-hydroxyhexanal, to oxamidation, optionally in the presence of an oxamidation catalyst or an oxamidation catalyst and promoter, to produce one or more substituted or unsubstituted hydroxyamides, e.g. 6-hydroxycaproamide, and/or one or more substituted or unsubstituted epsilon caprolactam precursors, e.g., 6-aminocaproamide, epsilon caprolactone, epsilon caprolactone oligomers and esters of 6-hydroxycaproic acid and mixtures thereof, and (b) subjecting said one or more substituted or unsubstituted hydroxyamides and/or said one or more substituted or unsubstituted epsilon caprolactam precursors to dehydration, optionally in the presence of a dehydration catalyst or a dehydration catalyst and promoter, and cyclization, optionally in the presence of a cyclization catalyst or a cyclization catalyst and promoter, to produce said one or more substituted or unsubstituted epsilon caprolactams; wherein the amount of byproducts resulting from reduction and/or reductive amination of said one or more substituted or unsubstituted hydroxyaldehydes, e.g., 1,6-hexanediol, aminohexanol, and the like, is no greater than about 10 weight percent, preferably no greater than about 5 weight percent, and more preferably no greater than about 1 weight percent, of the total of said one or more substituted or unsubstituted hydroxyamides and/or one or more substituted or unsubstituted epsilon caprolactam precursors.

This invention yet further relates in part to processes for producing one or more substituted or unsubstituted epsilon caprolactams, e.g., epsilon caprolactam, which comprise (a) subjecting one or more substituted or unsubstituted hydroxyaldehydes, e.g., 6-hydroxyhexanal, to oxidation, optionally in the presence of an oxidation catalyst or an oxidation catalyst and promoter, to produce one or more substituted or unsubstituted hydroxyacids, e.g. 6-hydroxycaproic acid, and/or one or more substituted or unsubstituted epsilon caprolactam precursors, e.g., epsilon caprolactone, epsilon caprolactone oligomers and esters of 6-hydroxycaproic acid and mixtures thereof, and (b) subjecting said one or more substituted or unsubstituted hydroxyacids and/or said one or more substituted or unsubstituted epsilon caprolactam precursors to amination, optionally in the presence of an amination catalyst or an amination catalyst and promoter, and cyclization, optionally in the presence of a cyclization catalyst or a cyclization catalyst and promoter, to produce said one or more substituted or unsubstituted epsilon caprolactams; wherein the amount of byproducts resulting from reduction and/or reductive amination of said one or more substituted or unsubstituted hydroxyaldehydes, e.g., 1,6-hexanediol, aminohexanol, and the like, is no greater than about 10 weight percent, preferably no greater than about 5 weight percent, and more preferably no greater than about 1 weight percent, of the total of said one or more substituted or unsubstituted hydroxyacids and/or one or more substituted or unsubstituted epsilon caprolactam precursors.

This invention also relates in part to processes for producing a batchwise or continuously generated reaction mixture comprising:

(1) one or more substituted or unsubstituted epsilon caprolactams, e.g., epsilon caprolactam;

(2) optionally one or more substituted or unsubstituted hydroxyamides, e.g., 6-hydroxycaproamide;

(3) optionally one or more substituted or unsubstituted epsilon caprolactam precursors, e.g., 6-aminocaproamide, epsilon caprolactone, epsilon caprolactone oligomers and esters of 6-hydroxycaproic acid and mixtures thereof; and (4) one or more substituted or unsubstituted hydroxyaldehydes, e.g., 6-hydroxyhexanal; wherein the weight ratio of component (1) to the sum of components (2), (3) and (4), is greater than about 0.1, preferably greater than about 0.25, more preferably greater than about 1.0; and the weight ratio of component (4) to the sum of components (1), (2) and (3) is about 0 to about 100, preferably about 0.001 to about 50; which processes comprise (a) subjecting one or more substituted or unsubstituted hydroxyaldehydes to oxamidation, optionally in the presence of an oxamidation catalyst or an oxamidation catalyst and promoter, to produce one or more substituted or unsubstituted hydroxyamides and/or one or more substituted or unsubstituted epsilon caprolactam precursors, and (b) subjecting said one or more substituted or unsubstituted hydroxyamides and/or said one or more substituted or unsubstituted epsilon caprolactam precursors to dehydration, optionally in the presence of a dehydration catalyst or a dehydration catalyst and promoter, and cyclization, optionally in the presence of a cyclization catalyst or a cyclization catalyst and promoter, to produce said batchwise or continuously generated reaction mixture; wherein the amount of byproducts resulting from reduction and/or reductive amination of said one or more substituted or unsubstituted hydroxyaldehydes, e.g., 1,6-hexanediol, aminohexanol, and the like, is no greater than about 10 weight percent, preferably no greater than about 5 weight percent, and more preferably no greater than about 1 weight percent, of the total of said one or more substituted or unsubstituted hydroxyamides and/or one or more substituted or unsubstituted epsilon caprolactam precursors.

This invention further relates in part to processes for producing a batchwise or continuously generated reaction mixture comprising:

(1) one or more substituted or unsubstituted epsilon caprolactams, e.g., epsilon caprolactam;

(2) optionally one or more substituted or unsubstituted hydroxyacids, e.g., 6-hydroxycaproic acid;

(3) optionally one or more substituted or unsubstituted epsilon caprolactam precursors, e.g., epsilon caprolactone, epsilon caprolactone oligomers and esters of 6-hydroxycaproic acid and mixtures thereof; and (4) one or more substituted or unsubstituted hydroxyaldehydes, e.g., 6-hydroxyhexanal; wherein the weight ratio of component (1) to the sum of components (2), (3) and (4), is greater than about 0.1, preferably greater than about 0.25, more preferably greater than about 1.0; and the weight ratio of component (4) to the sum of components (1), (2) and (3) is about 0 to about 100, preferably about 0.001 to about 50; which processes comprise (a) subjecting one or more substituted or unsubstituted hydroxyaldehydes to oxidation, optionally in the presence of an oxidation catalyst or an oxidation catalyst and promoter, to produce one or more substituted or unsubstituted hydroxyacids and/or one or more substituted or unsubstituted epsilon caprolactam precursors, and (b) subjecting said one or more substituted or unsubstituted hydroxyacids and/or said one or more substituted or unsubstituted epsilon caprolactam precursors to amination, optionally in the presence of an amination catalyst or an amination catalyst and promoter, and cyclization, optionally in the presence of a cyclization catalyst or a cyclization catalyst and promoter, to produce said batchwise or continuously generated reaction mixture; wherein the amount of byproducts resulting from reduction and/or reductive amination of said one or more substituted or unsubstituted hydroxyaldehydes, e.g., 1,6-hexanediol, aminohexanol, and the like, is no greater than about 10 weight percent, preferably no greater than about 5 weight percent, and more preferably no greater than about 1 weight percent, of the total of said one or more substituted or unsubstituted hydroxyacids and/or one or more substituted or unsubstituted epsilon caprolactam precursors.

This invention yet further relates in part to processes for producing a reaction mixture comprising one or more substituted or unsubstituted epsilon caprolactams, e.g., epsilon caprolactam, which processes comprise (a) subjecting one or more substituted or unsubstituted hydroxyaldehydes, e.g., 6-hydroxyhexanal, to oxamidation, optionally in the presence of an oxamidation catalyst or an oxamidation catalyst and promoter, to produce one or more substituted or unsubstituted hydroxyamides, e.g. 6-hydroxycaproamide, and/or one or more substituted or unsubstituted epsilon caprolactam precursors, e.g., 6-aminocaproamide, epsilon caprolactone, epsilon caprolactone oligomers and esters of 6-hydroxycaproic acid and mixtures thereof, and (b) subjecting said one or more substituted or unsubstituted hydroxyamides and/or said one or more substituted or unsubstituted epsilon caprolactam precursors to dehydration, optionally in the presence of a dehydration catalyst or a dehydration catalyst and promoter, and cyclization, optionally in the presence of a cyclization catalyst or a cyclization catalyst and promoter, to produce said reaction mixture comprising one or more substituted or unsubstituted epsilon caprolactams; wherein the amount of byproducts resulting from reduction and/or reductive amination of said one or more substituted or unsubstituted hydroxyaldehydes, e.g., 1,6-hexanediol, aminohexanol, and the like, is no greater than about 10 weight percent, preferably no greater than about 5 weight percent, and more preferably no greater than about 1 weight percent, of the total of said one or more substituted or unsubstituted hydroxyamides and/or one or more substituted or unsubstituted epsilon caprolactam precursors.

This invention also relates in part to processes for producing a reaction mixture comprising one or more substituted or unsubstituted epsilon caprolactams, e.g., epsilon caprolactam, which processes comprise (a) subjecting one or more substituted or unsubstituted hydroxyaldehydes, e.g., 6-hydroxyhexanal, to oxidation, optionally in the presence of an oxidation catalyst or an oxidation catalyst and promoter, to produce one or more substituted or unsubstituted hydroxyacids, e.g. 6-hydroxycaproic acid, and/or one or more substituted or unsubstituted epsilon caprolactam precursors, e.g., epsilon caprolactone, epsilon caprolactone oligomers and esters of 6-hydroxycaproic acid and mixtures thereof, and (b) subjecting said one or more substituted or unsubstituted hydroxyacids and/or said one or more substituted or unsubstituted epsilon caprolactam precursors to amination, optionally in the presence of an amination catalyst or an amination catalyst and promoter, and cyclization, optionally in the presence of a cyclization catalyst or a cyclization catalyst and promoter, to produce said reaction mixture comprising one or more substituted or unsubstituted epsilon caprolactams; wherein the amount of byproducts resulting from reduction and/or reductive amination of said one or more substituted or unsubstituted hydroxyaldehydes, e.g., 1,6-hexanediol, aminohexanol, and the like, is no greater than about 10 weight percent, preferably no greater than about 5 weight percent, and more preferably no greater than about 1 weight percent, of the total of said one or more substituted or unsubstituted hydroxyacids and/or one or more substituted or unsubstituted epsilon caprolactam precursors.

The processes of this invention can achieve high selectivities of 6-hydroxyhexanals to epsilon caprolactams. Selectivities of 6-hydroxyhexanal to epsilon caprolactam of at least 10% by weight and up to 75% by weight or greater may be achieved by the processes of this invention. The high selectivities are attainable by controlling the amount of undesirable byproducts resulting from reduction and/or reductive amination of the hydroxyaldehyde starting materials, e.g., diols, ethers, diamines, aminoalcohols and the like.

This invention further relates in part to a batchwise or continuously generated reaction mixture comprising:

(1) one or more substituted or unsubstituted epsilon caprolactams, e.g., epsilon caprolactam;

(2) optionally one or more substituted or unsubstituted hydroxyamides, e.g., 6-hydroxycaproamide;

(3) optionally one or more substituted or unsubstituted epsilon caprolactam precursors, e.g., 6-aminocaproamide, epsilon caprolactone oligomers and esters of 6-hydroxycaproic acid and mixtures thereof; and (4) one or more substituted or unsubstituted hydroxyaldehydes, e.g., 6-hydroxyhexanal; wherein the weight ratio of component (1) to the sum of components (2), (3) and (4), is greater than about 0.1, preferably greater than about 0.25, more preferably greater than about 1.0; and the weight ratio of component (4) to the sum of components (1), (2) and (3) is about 0 to about 100, preferably about 0.001 to about 50.

This invention yet further relates in part to a batchwise or continuously generated reaction mixture comprising:

(1) one or more substituted or unsubstituted epsilon caprolactams, e.g., epsilon caprolactam;

(2) optionally one or more substituted or unsubstituted hydroxyacids, e.g., 6-hydroxycaproic acid;

(3) optionally one or more substituted or unsubstituted epsilon caprolactam precursors, e.g., epsilon caprolactone, epsilon caprolactone oligomers and esters of 6-hydroxycaproic acid and mixtures thereof; and (4) one or more substituted or unsubstituted hydroxyaldehydes, e.g., 6-hydroxyhexanal;
wherein the weight ratio of component (1) to the sum of components (2), (3) and (4), is greater than about 0.1, preferably greater than about 0.25, more preferably greater than about 1.0; and the weight ratio of component (4) to the sum of components (1), (2) and (3) is about 0 to about 100, preferably about 0.001 to about 50.

This invention also relates in part to a reaction mixture comprising one or more substituted or unsubstituted epsilon caprolactams, e.g., epsilon caprolactam, in which said reaction mixture is prepared by a process which comprises: (a) subjecting one or more substituted or unsubstituted hydroxyaldehydes, e.g., 6-hydroxyhexanal, to oxamidation, optionally in the presence of an oxamidation catalyst or an oxamidation catalyst and promoter, to produce one or more substituted or unsubstituted hydroxyamides, e.g. 6-hydroxycaproamide, and/or one or more substituted or unsubstituted epsilon caprolactam precursors, e.g., 6-aminocaproamide, epsilon caprolactone, epsilon caprolactone oligomers and esters of 6-hydroxycaproic acid and mixtures thereof, and (b) subjecting said one or more substituted or unsubstituted hydroxyamides and/or said one or more substituted or unsubstituted epsilon caprolactam precursors to dehydration, optionally in the presence of a dehydration catalyst or a dehydration catalyst and promoter, and cyclization, optionally in the presence of a cyclization catalyst or a cyclization catalyst and promoter, to produce said reaction mixture comprising one or more substituted or unsubstituted epsilon caprolactams; wherein the amount of byproducts resulting from reduction and/or reductive amination of said one or more substituted or unsubstituted hydroxyaldehydes, e.g., 1,6-hexanediol, aminohexanol, and the like, is no greater than about 10 weight percent, preferably no greater than about 5 weight percent, and more preferably no greater than about 1 weight percent, of the total of said one or more substituted or unsubstituted hydroxyamides and/or one or more substituted or unsubstituted epsilon caprolactam precursors.

This invention further relates in part to a reaction mixture comprising one or more substituted or unsubstituted epsilon caprolactams, e.g., epsilon caprolactam, in which said reaction mixture is prepared by a process which comprises: (a) subjecting one or more substituted or unsubstituted hydroxyaldehydes, e.g., 6-hydroxyhexanal, to oxidation, optionally in the presence of an oxidation catalyst or an oxidation catalyst and promoter, to produce one or more substituted or unsubstituted hydroxyacids, e.g. 6-hydroxycaproic acid, and/or one or more substituted or unsubstituted epsilon caprolactam precursors, e.g., epsilon caprolactone, epsilon caprolactone oligomers and esters of 6-hydroxycaproic acid and mixtures thereof, and (b) subjecting said one or more substituted or unsubstituted hydroxyacids and/or said one or more substituted or unsubstituted epsilon caprolactam precursors to amination, optionally in the presence of an amination catalyst or an amination catalyst and promoter, and cyclization, optionally in the presence of a cyclization catalyst or a cyclization catalyst and promoter, to produce said reaction mixture comprising one or more substituted or unsubstituted epsilon caprolactams; wherein the amount of byproducts resulting from reduction and/or reductive amination of said one or more substituted or unsubstituted hydroxyaldehydes, e.g., 1,6-hexanediol, aminohexanol, and the like, is no greater than about 10 weight percent, preferably no greater than about 5 weight percent, and more preferably no greater than about 1 weight percent, of the total of said one or more substituted or unsubstituted hydroxyacids and/or one or more substituted or unsubstituted epsilon caprolactam precursors.

The reaction mixtures of this invention are distinctive insofar as the processes for their preparation achieve the generation of high selectivities of epsilon caprolactams in a manner which can be suitably employed in a commercial process for the manufacture of epsilon caprolactam. In particular, the reaction mixtures of this invention are distinctive insofar as the processes for their preparation allow for the production of epsilon caprolactams in relatively high yields without generating large amounts of byproducts such as those resulting from reduction and/or reductive amination of the hydroxyaldehyde starting materials, e.g., diols, ethers, diamines, aminoalcohols, and the like.

DETAILED DESCRIPTION
Oxamidation Step or Stage

The oxamidation process involves converting one or more substituted or unsubstituted hydroxyaldehydes, e.g., 6-hydroxyhexanal, to one or more substituted or unsubstituted hydroxyamides, e.g., 6-hydroxycaproamide, and/or one or more substituted or unsubstituted epsilon caprolactam precursors in one or more steps or stages. In this conversion, the amount of byproducts resulting from reduction and/or reductive amination of one or more substituted or unsubstituted hydroxyaldehydes, e.g., diols such as 1,6-hexanediol, ethers and their oligomers, diamines such as hexamethylenediamine, imines such as hexamethyleneimine, aminoalcohols such as aminohexanol, and their oligomers, is no greater than about 10 weight percent, preferably no greater than about 5 weight percent, and more preferably no greater than about 1 weight percent, of the total of the one or more substituted or unsubstituted hydroxyamides and/or one or more substituted or unsubstituted epsilon caprolactam precursors. As used herein, the term "oxamidation" is contemplated to include, but is not limited to, all permissible oxamidation processes involve converting one or more substituted or unsubstituted hydroxyaldehydes to one or more substituted or unsubstituted hydroxyamides, and/or one or more substituted or unsubstituted epsilon caprolactam precursors. In general, the oxamidation step or stage comprises reacting one or more substituted or unsubstituted hydroxyaldehydes with oxygen and an amine or ammonia, optionally in the presence of an oxamidation catalyst or an oxamidation catalyst and promoter, to produce one or more substituted or unsubstituted hydroxyamides and/or one or more substituted or unsubstituted epsilon caprolactam precursors.

The substituted and unsubstituted hydroxyaldehyde starting materials useful in the oxamidation stage or step include, but are not limited to, 6-hydroxyhexanals such as 6-hydroxyhexanal and substituted 6-hydroxyhexanals (e.g., 2-methyl-6-hydroxyhexanal and 3,4-dimethyl-6-hydroxyhexanal) and the like, including mixtures of one or more of the above 6-hydroxyhexanals. Illustrative of suitable substituted and unsubstituted hydroxyaldehydes (including derivatives of hydroxyaldehydes) include those permissible substituted and unsubstituted hydroxyaldehydes which are described in Beilsteins Handbuch der Organischen Chemie, Springer Verlag KG, 4$^{th}$ Edition, the pertinent portions of which are incorporated herein by reference. As used herein, the term "hydroxyaldehydes" is contemplated to include, but is not limited to, 6-hydroxyhexanals and/or their cyclic lactols, hydrates or oligomers. Processes for the preparation of substituted and unsubstituted hydroxyaldehydes suitable for use as starting material(s) in this invention are disclosed in U.S. Pat. Nos. 5,821,389 and 5,817,883, the disclosures of which are incorporated herein by reference.

The hydroxyaldehyde starting materials preferably contain little or none of the undesirable byproducts described herein, e.g., diols, ethers, diamines, aminoalcohols, and the like. The amount of hydroxyaldehydes employed in the oxamidation step is not narrowly critical and can be any amount sufficient to produce hydroxyamides and/or epsilon caprolactam precursors, preferably in high selectivities.

The oxamidation process may be carried out in one or more steps or stages and in any permissible sequence of steps or stages. In a one step process, hydroxyamides and/or epsilon caprolactam precursors are the desired products leaving the reaction zone. In a multistep or multistage process, intermediate products are the major products leaving the individual reaction zones. For example, in a two stage process, a hydroxyaldehyde, e.g., 6-hydroxyhexanal, may be converted directly to an acid, e.g., 6-hydroxycaproic acid, in a first stage, and the acid may be converted to an amide, e.g., 6-hydroxycaproamide, in a second stage. Of course some overlap of these individual transformations may occur, so that in a two stage process, some amination may occur in the first stage.

The particular oxamidation reaction conditions are not narrowly critical and can be any effective oxamidation conditions sufficient to produce hydroxyamides and/or epsilon caprolactam precursors. The reactors may be stirred tanks, tubular reactors and the like. The exact reaction conditions will be governed by the best compromise between achieving high selectivity, activity lifetime and ease of operability, as well as the intrinsic reactivity of the hydroxyamides and/or epsilon caprolactam precursors in question and the stability of the hydroxyamides and/or epsilon caprolactam precursors to the reaction conditions. Products may be recovered after a particular reaction zone and purified if desired although they may be introduced to the next reaction zone without purification. Recovery and purification may be by any appropriate means, which will largely be determined by the particular hydroxyaldehyde employed.

The oxamidation reaction can be conducted at a temperature of from about 0° C. to about 400° C. for a period of about 1 minute or less to about 4 hours or longer with the longer time being used at the lower temperature, preferably from about 10° C. to about 150° C. for about 1 minute or less to about 2 hours or longer, and more preferably at about 20° C. to about 125° C. for about 1 hour or less. The temperature should be sufficient for reaction to occur (which may vary with catalyst system) but not so high as to cause hydroxyamide decomposition or polymerization.

The oxamidation reaction can be conducted over a wide range of pressures ranging from about 20 psig to about 2000 psig. It is preferable to conduct the oxamidation reaction at pressures of from about 100 psig to about 1000 psig. The oxamidation reaction is preferably effected in the liquid or vapor states or mixtures thereof. The total pressure will depend on the temperature and other reaction conditions.

Ammonia is preferably employed as the aminating agent in these reactions in conventional amounts, preferably in excess amounts, and it may be fed to the reactor in a variety of ways, including as a liquid, and a gas, in solution in for example water, or as ammonium salts in solution or in some other appropriate manner. Any excess ammonia may be separated off after oxamidation is completed. The hydroxyaldehydes may be fed to the reactor in any convenient manner, such as in solution, or as a neat liquid or solid.

Some of the reaction steps or stages may involve the use of a catalyst. Such catalysts are known in the art for traditional reactions, e.g., ammoxidation and oxidation, and can be homogeneous or heterogeneous. Catalysts useful in the oxamidation stage or step include, for example, palladium supported on carbon, palladium on supports such as alumina or silica, platinum on carbon, alkali metal hydroxide, cobalt acetate, manganese acetate, bismuth molybdates, molybdenum-vanadium oxides, manganese porphyrin complexes, homogeneous molybdenum complexes, and the like. See, for example, U.S. Pat. Nos. 5,288,744 and 4,414,134, the disclosures of which are incorporated herein by reference. Of course mixtures of oxamidation catalysts can also be employed if desired. The amount of catalyst employed will be dependent on the oxamidation reaction conditions employed and the amount should be sufficient to obtain the desired selectivity and degree of conversion. In general, the amount of catalyst employed should be sufficient to enable a conversion of hydroxyaldehyde to hydroxyamide of at least about 5 percent, preferably at least about 20 percent, and more preferably at least about 50 percent.

The oxamidation process may also be conducted in the presence of a promoter. As used herein, the term "promoter", when used in the context of oxamidation, means a material added to the oxamidation reaction mixture to impart a promotion effect to catalytic activity, e.g., rate, product selectivity, and/or catalyst stability (mechanical or dimensional strength of the catalyst). Illustrative promoters include, for example, alkali metal hydroxide, acetate salts, Group VII metals, rare earth oxides, alkaline earth metals, and the like. The promoter may be present in the oxamidation reaction mixture either alone or incorporated into the catalyst structure. The desired promoter will depend on the nature of the catalysts. The amount of promoter employed will depend upon the details of the catalyst system employed.

The oxamidation process may also be conducted in the presence of an initiator. As used herein, the term "initiator", when used in the context of oxamidation, means a material added to the oxamidation reaction mixture to initiate the reaction by starting, for example, a free radical chain reaction. Illustrative initiators include, for example, sodium persulfate, ammonium persulfate, benzoyl peroxide, perbenzoic acid, tertiary-butyl hydroperoxide, alkyl peroxide, peracids, peresters, azobisisobutyronitrile, redox systems such as hydrogen peroxide/iron acetate, and the like. The initiator may be present in the oxamidation reaction mixture either alone or in addition to a catalyst. The desired initiator will depend on the nature of the reaction system and reaction conditions. The amount of initiator employed will depend upon the details of the reaction system employed.

Illustrative substituted and unsubstituted hydroxyamide intermediates that can be prepared by the oxamidation stage or step of this invention include one or more of the following: hydroxyamides such as 6-hydroxycaproamide, 5-hydroxy-2-methylvaleramide and 4-hydroxy-2-ethylbutyramide, including mixtures comprising one or more of the above hydroxyamides. The preferred hydroxyamides have at least 6 carbon atoms. Illustrative epsilon caprolactam precursors include one or more of the following: hydroxyamides such as 6-hydroxycaproamide, aminoalcohols such as aminohexanol, iminoacids such as iminocaproic acid, aminoacids such as aminocaproic acid, imines, hemiaminals, imides, formylamides, aminoamides, amides or amines derived from hydroxyacids, and the corresponding dimers, trimers and oligomers, and the like. Illustrative of suitable substituted and unsubstituted hydroxyamides (including derivatives of hydroxyamides) and epsilon caprolactam precursors include those permissible substituted and unsubstituted hydroxyamides and epsilon caprolactam precursors which are described in Beilsteins Handbuch der Organischen Chemie, Springer Verlag KG, $4^{th}$ Edition, the pertinent portions of which are incorporated herein by reference.

Recovery and purification of hydroxyamides may be by any appropriate means, and may include distillation, phase separation, extraction, precipitation, absorption, crystallization, membrane separation, derivative formation and other suitable means. For example, a crude reaction product can be subjected to a distillation-separation at atmospheric or reduced pressure through a packed distillation column. Reactive distillation may be useful in conducting the oxamidation reaction. The subsequent derivatizations of the hydroxyamide and caprolactam precursors may be conducted without the need to separate the hydroxyamide and caprolactam precursors from the other components of the crude reaction mixtures.

Oxidation Stage or Step

The oxidation stage or step of this invention involves converting one or more substituted or unsubstituted hydroxyhexanals to one or more substituted or unsubstituted hydroxyacids and/or one or more substituted or unsubstituted epsilon caprolactam precursors. In this conversion, the amount of byproducts resulting from reduction and/or reductive amination of one or more substituted or unsubstituted hydroxyaldehydes, e.g., diols such as 1,6-hexanediol, ethers and their oligomers, diamines such as hexamethylenediamine, imines such as hexamethyleneimine, aminoalcohols such as aminohexanol, and their oligomers, is no greater than about 10 weight percent, preferably no greater than about 5 weight percent, and more preferably no greater than about 1 weight percent, of the total of the one or more substituted or unsubstituted hydroxyacids and/or one or more substituted or unsubstituted epsilon caprolactam precursors. The oxidation stage or step of this invention may be conducted in one or more steps or stages, preferably a one step process.

As used herein, the term "oxidation" is contemplated to include all permissible oxidation processes which involve converting one or more substituted or unsubstituted hydroxyhexanals to one or more substituted or unsubstituted hydroxyacids and/or one or more substituted or unsubstituted epsilon caprolactam precursors. In general, the oxidation step or stage comprises reacting one or more substituted or unsubstituted hydroxyhexanals, e.g., 6-hydroxyhexanal, with an oxygen source, e.g., air, essentially pure oxygen or oxygen-enriched air containing, for example, about 50% oxygen, optionally in the presence of an oxidation catalyst or an oxidation catalyst and a promoter, and optionally an initiator, to produce one or more substituted or unsubstituted hydroxyacids and/or one or more substituted or unsubstituted epsilon caprolactam precursors.

Hydroxyaldehydes useful in the oxidation process are described above and can be prepared by the methods described above. The amount of hydroxyaldehydes employed in the oxidation step is not narrowly critical and can be any amount sufficient to produce hydroxyacids and/or epsilon caprolactam precursors, preferably in high selectivities.

The oxidation process may be carried out in one or more steps or stages and in any permissible sequence of steps or stages. In a one step process, hydroxyacids and/or epsilon caprolactam precursors are the desired products leaving the reaction zone. In a multistep or multistage process, intermediate products are the major products leaving the individual reaction zones. Of course some overlap of individual transformations may occur, so that in a two stage process, some transformations may occur in different order.

The particular oxidation reaction conditions are not narrowly critical and can be any effective oxidation conditions sufficient to produce hydroxyacids and/or epsilon caprolactam precursors. The reactors may be stirred tanks, tubular reactors and the like. The exact reaction conditions will be governed by the best compromise between achieving high selectivity, activity, lifetime and ease of operability, as well as the intrinsic reactivity of the hydroxyacids and/or epsilon caprolactam precursors in question and the stability of the hydroxyacids and/or epsilon caprolactam precursors to the reaction conditions. Illustrative of certain reaction conditions that may be employed in the oxidation processes are described, for example, in U.S. Pat. Nos. 5,831,121, 5,840,959, 4,537,987 and 5,817,870, the disclosures of which are incorporated herein by reference. Products may be recovered after a particular reaction zone and purified if desired although they may be introduced to the next reaction zone without purification. Recovery and purification may be by any appropriate means, which will largely be determined by the particular hydroxyaldehyde starting material employed.

The oxidation reaction can be conducted at a temperature of from about 0° C. to about 200° C. for a period of about 1 minute or less to about 4 hours or longer with the longer time being used at the lower temperature, preferably from about 10° C. to about 150° C. for about 1 minute or less to about 2 hours or longer, and more preferably at about 20° C. to about 125° C. for about 1 hour or less. The temperature should be sufficient for reaction to occur (which may vary with catalyst system) but not so high as to cause hydroxyacid decomposition or polymerization.

The oxidation reaction can be conducted over a wide range of pressures ranging from about 20 psig to about 2000 psig. It is preferable to conduct the oxidation reaction at pressures of from about 100 psig to about 1000 psig. The oxidation reaction is preferably effected in the liquid or vapor states or mixtures thereof. The total pressure will depend on the temperature and other reaction conditions.

The oxidation reaction can be conducted using a variety of oxidants. Illustrative oxidants include, for example, molecular oxygen, molecular oxygen mixed with an inert gas such as nitrogen, molecular oxygen in air, hydrogen peroxide, peracetic acid and the like. The oxidant can be employed in conventional amounts.

The oxidation step or stage may involve the use of a catalyst. Such catalysts are known in the art and can be homogeneous or heterogeneous. Catalysts useful in the oxidation stage or step include, for example, palladium supported on carbon, palladium on supports such as alumina or silica, platinum on carbon, alkali metal hydroxide, cobalt acetate, manganese acetate, bismuth molybdates, molybdenum-vanadium oxides, manganese porphyrin complexes, homogeneous molybdenum complexes, and the like. See, for example, U.S. Pat. Nos. 4,596,787 and 5,864,051, the disclosures of which are incorporated herein by reference. Of course mixtures of oxidation catalysts can also be employed if desired. The amount of catalyst employed will be dependent on the oxidation reaction conditions employed and the amount should be sufficient to obtain the desired selectivity and degree of conversion. In general, the amount of catalyst employed should be sufficient to enable a conversion of hydroxyaldehyde to hydroxyacid of at least about 5 percent, preferably at least about 20 percent, and more preferably at least about 50 percent.

The oxidation process may also be conducted in the presence of a promoter. As used herein, the term "promoter", when used in the context of oxidation, means a material added to the oxidation reaction mixture to impart a promotion effect to catalytic activity, e.g., rate, product selectivity, and/or catalyst stability (mechanical or dimensional strength of the catalyst). Illustrative promoters include, for example, alkali metal hydroxide, acetate salts, Group VII metals, rare earth oxides, alkaline earth metals, and the like. The promoter may be present in the oxidation reaction mixture either alone or incorporated into the catalyst structure. The desired promoter will depend on the nature of the catalysts. The amount of promoter employed will depend upon the details of the catalyst system employed.

The oxidation process may also be conducted in the presence of an initiator. As used herein, the term "initiator", when used in the context of oxidation, means a material added to the oxidation reaction mixture to initiate the reaction by starting, for example, a free radical chain reaction. Illustrative initiators include, for example, sodium persulfate, ammonium persulfate, benzoyl peroxide, perbenzoic acid, tertiary-butyl hydroperoxide, alkyl peroxide, peracids, peresters, azobisisobutyronitrile, redox systems such as hydrogen peroxide/iron acetate, and the like. The initiator may be present in the oxidation reaction mixture either alone or in addition to a catalyst. The desired initiator will depend on the nature of the reaction system and reaction conditions. The amount of initiator employed will depend upon the details of the reaction system employed.

Illustrative substituted and unsubstituted hydroxyacid intermediates that can be prepared by the oxidation stage or step of this invention include one or more of the following: hydroxyacids such as 6-hydroxycaproic acid, 5-hydroxy-2-methylvaleric acid and 4-hydroxy-2-ethylbutyric acid, including mixtures comprising one or more of the above hydroxyacids. The preferred hydroxyacids have at least 6 carbon atoms. Illustrative epsilon caprolactam precursors include one or more of the following: hydroxyacids such as 6-hydroxycaproic acid, caprolactone, adipic acid, formylvaleric acid, caprolactone oligomers, esters of hydroxyacids such as esters of 6-hydroxycaproic acid, and the like. Illustrative of suitable substituted and unsubstituted hydroxyacids (including derivatives of hydroxyacids) and epsilon caprolactam precursors include those permissible substituted and unsubstituted hydroxyacids and epsilon caprolactam precursors which are described in Beilsteins Handbuch der Organischen Chemie, Springer Verlag KG, $4^{th}$ Edition, the pertinent portions of which are incorporated herein by reference.

Recovery and purification of hydroxyacids may be by any appropriate means, and may include distillation, phase separation, extraction, precipitation, absorption, crystallization, membrane separation, derivative formation and other suitable means. For example, a crude reaction product can be subjected to a distillation-separation at atmospheric or reduced pressure through a packed distillation column. Reactive distillation may be useful in conducting the oxidation reaction. The subsequent amination and cyclization of the hydroxyacid and caprolactam precursors may be conducted without the need to separate the hydroxyacid and caprolactam precursors from the other components of the crude reaction mixtures.

In an embodiment, the oxidation stage or step of this invention may be carried out in a liquid oxidation reactor such as described, for example, in copending U.S. patent application Ser. No. 09/063,675, filed on Apr. 21, 1998, the disclosure of which is incorporated herein by reference.

Amination and Cyclization Steps or Stages

The amination and cyclization processes involve converting one or more substituted or unsubstituted hydroxyacids, e.g., 6-hydroxycaproic acid, and/or one or more substituted or unsubstituted epsilon caprolactam precursors to one or more substituted or unsubstituted epsilon caprolactams in one or more steps or stages. As used herein, the term "lamination" is contemplated to include, but is not limited to, all permissible amination processes (including, but not limited to, reductive amination and oxidative amination) which in conjunction with cyclization involve converting one or more substituted or unsubstituted hydroxyacids and/or one or more substituted or unsubstituted epsilon caprolactam precursors to one or more substituted or unsubstituted epsilon caprolactams. As used herein, the term "cyclization", when used in the context of amination, is contemplated to include, but is not limited to, all permissible cyclization processes which in conjunction with amination involve converting one or more substituted or unsubstituted hydroxyacids and/or one or more substituted or unsubstituted epsilon caprolactam precursors to one or more substituted or unsubstituted epsilon caprolactams. In general, the amination and cyclization steps or stages comprise reacting one or more substituted or unsubstituted hydroxyacids and/or one or more substituted or unsubstituted epsilon caprolactam precursors with an amine or ammonia, optionally in the presence of one or more catalysts or one or more catalysts and promoters, to produce one or more substituted or unsubstituted epsilon caprolactams.

Hydroxyacids and/or epsilon caprolactam precursors useful in the amination and cyclization processes are known materials and can be prepared by the oxidation steps described above or by other conventional processes. Reaction mixtures comprising hydroxyacids and/or epsilon caprolactam precursors may be useful herein. The amounts of hydroxyacids and/or epsilon caprolactam precursors employed in the amination and cyclization steps are not narrowly critical and can be any amounts sufficient to produce epsilon caprolactam, preferably in high selectivities.

The amination and cyclization processes may be carried out in one or more steps or stages and in any permissible sequence of steps or stages. In a one step process, epsilon caprolactam is the desired product leaving the reaction zone. In a multistep or multistage process, intermediate products are the major products leaving the individual reaction zones. For example, in a three stage process, an epsilon caprolactam precursor, e.g., 6-hydroxycaproic acid, may be converted to an imine in a first stage, the imine may be hydrogenated to an amine in a second stage, e.g., 6-aminocaproic acid, and the amine may be cyclized to epsilon caprolactam in a third stage. In a two stage process, an epsilon caprolactam precursor, e.g., 6-hydroxycaproic acid, may be converted directly to an amide, e.g., 6-aminocaproamide, in a first stage, and the amide may be dehydrated/cyclized to epsilon caprolactam in a second stage. Of course some overlap of these individual transformations may occur, so that in a two stage process, some cyclization may occur in the first stage.

The particular amination and cyclization reaction conditions are not narrowly critical and can be any effective amination and cyclization conditions sufficient to produce the epsilon caprolactam. The reactors may be stirred tanks, tubular reactors and the like. The exact reaction conditions will be governed by the best compromise between achieving high catalyst selectivity, activity, lifetime and ease of operability, as well as the intrinsic reactivity of the hydroxyacids and/or epsilon caprolactam precursors in question and the stability of the hydroxyacids and/or epsilon caprolactam precursors and the desired reaction product to the reaction conditions. Illustrative of certain reaction conditions that may be employed in the amination and/or cyclization processes are described, for example, in U.S. Pat. Nos. 4,730,041, 4,731,445 and 5,068,398, the disclosures of which are incorporated herein by reference. Products may be recovered after a particular reaction zone and purified if desired although they may be introduced to the next reaction zone without purification. Recovery and purification may be by any appropriate means, which will largely be determined by the particular epsilon caprolactam precursor employed.

The amination reaction can be conducted at a temperature of from about 0° C. to about 400° C. for a period of about 1 minute or less to about 4 hours or longer with the longer time being used at the lower temperature, preferably from about 50° C. to about 300° C. for about 1 minute or less to about 2 hours or longer, and more preferably at about 100° C. to about 250° C. for about 1 hour or less. The temperature should be sufficient for reaction to occur (which may vary with catalyst system) but not so high as to cause hydroxyacid decomposition or polymerization.

The amination reaction can be conducted over a wide range of pressures ranging from about 20 psig to about 4500 psig. It is preferable to conduct the amination reaction at pressures of from about 100 psig to about 2000 psig. The amination reaction is preferably effected in the liquid or vapor states or mixtures thereof. The total pressure will depend on the catalyst system used. A minimum hydrogen partial pressure can be chosen to maximize the lifetime of the amination catalyst.

Ammonia is preferably employed as the aminating agent in these reactions in conventional amounts, preferably in excess amounts, and it may be fed to the reactor in a variety of ways, including as a liquid, and a gas, in solution in for example water, or as ammonium salts in solution or in some other appropriate manner, e.g., urea. Any excess ammonia is preferably separated off after amination is completed. The hydroxyacids and/or epsilon caprolactam precursors may be fed to the reactor in any convenient manner, such as in solution, or as a neat liquid.

Some of the reaction steps or stages may involve the use of a catalyst. Such catalysts are known in the art and can be used in conventional amounts. For example, the hydrogenation of an imine to an amine may advantageously employ an appropriate hydrogenation catalyst.

Catalysts useful in the amination stage or step are conventional materials and include, for example, heterogeneous catalysts such as acidic, basic or amphoteric oxides of Group IIA, IIIA and IVA metals, e.g., calcium oxide, magnesium oxide, boron oxide, alumina, tin oxide or silica, pyrogenic silica, silica gel, kieselguhr, quartz or mixtures thereof, and oxides of metals of Group IVB, VB, VIB, IB and IIB such as titanium oxide in amorphous form or as anatase or rutile, zirconium oxide, zinc oxide, manganese oxide or mixtures thereof. See, for example, U.S. Pat. No. 4,730,041, supra, and U.S. Pat. Nos. 5,495,014 and 5,646,277, the disclosures of which are incorporated herein by reference. Other catalysts useful in the amination stage or step include nickel-rhenium catalysts supported on certain materials, e.g., silica, silica-alumina, alpha-alumina, silica-titania, and kieselguhrs or diatomaceous earths. Such supported nickel-rhenium catalysts may contain boron or other metals in combination therewith, e.g., Ni—Re—B, Ni—Re—Ca, Ni—Re—Mg, Ni—Re—W, Ni—Re—Fe, Ni—Re—Zn, and the like. See, for example, U.S. Pat. Nos. 4,123,462, 5,750,790 and 5,891,820, the disclosures of which are incorporated herein by reference. Homogeneous catalysts may also be employed if desired. Of course mixtures of amination and cyclization catalysts can also be employed if desired. The amount of catalyst employed will be dependent on the amination and cyclization reaction conditions employed and the amount should be sufficient to obtain the desired selectivity and degree of conversion. In general, the amount of catalyst employed should be sufficient to enable a conversion of hydroxyacid and/or epsilon caprolactam precursors to epsilon caprolactam of at least about 5 percent, preferably at least about 20 percent, and more preferably at least about 50 percent.

The amination process may also be conducted in the presence of a promoter. As used herein, the term "promoter", when used in the context of amination, means a material added to the amination reaction mixture to impart a promotion effect to catalytic activity, e.g., rate, product selectivity, and/or catalyst stability (mechanical or dimensional strength of the catalyst). Illustrative promoters include, for example, alkali metal hydroxide, acetate salts, Group VII metals, rare earth oxides, alkaline earth metals, and the like. The promoter may be present in the amination reaction mixture either alone or incorporated into the catalyst structure. The desired promoter will depend on the nature of the catalysts. The amount of promoter employed will depend upon the details of the catalyst system employed.

As indicated above, a possible transformation in the reaction sequence is the reduction of imine to amine functionality, i.e., hydrogenation reaction. This transformation may be carried out using a variety of known catalysts, such as hydrogenation or dehydrogenation catalysts, in conventional amounts. See, for example, U.S. Pat. Nos. 4,730,041, 5,646,277, 5,495,014, 4,123,462, 5,750,790 and 5,891,820, supra. Such catalysts comprise a variety of materials, including homogeneous and heterogeneous catalysts, such as palladium, ruthenium, platinum, rhodium, copper chromite, nickel, copper, cobalt, and the like. These metal catalysts can be supported on a variety of supports, including titania, magnesium silicate, alumina, vanadia and the like, and may be further promoted by additional metals or other additives, for example, barium, manganese, zirconium, selenium, calcium, molybdenum, cobalt, and the like. Other illustrative catalysts comprise a variety of materials, including homogeneous and heterogeneous catalysts, or other Group 8, 9 and 10 metals, copper, chromium oxide, and a variety of metal nitrides and carbides, and the like. These metal catalysts can be supported on a variety of supports, including titania, lanthanum oxide, ceria, silicon carbide, magnesium silicate, aluminas, silica-aluminas, vanadia and the like, and may be further promoted by additional metals or other additives, for example, barium, manganese, zirconium, selenium, calcium, molybdenum, cobalt or other Group 8, 9 and 10 metals, copper, iron, and zinc. A variety of homogeneous catalysts may also be employed, for example rhodium, ruthenium, cobalt, nickel and the like. Such catalysts can be promoted or stabilized by a variety of ligands including nitrogen or phosphorus containing materials such amines, phosphines, phosphites and similar materials.

The hydrogenation reaction may be carried out in any desired manner, for example in a tubular or a stirred tank reactor, and the like. The hydrogenation reaction can be carried out by conventional methods. For example, reaction temperatures may range from about 0° C. to about 400° C. or higher, preferably from about 50° C. to about 300° C. for a period of about 1 minute or less to about 4 hours or longer with the longer time being used at the lower temperature.

The hydrogenation reaction can be conducted over a wide range of pressures ranging from 20 psig to about 4500 psig. It is preferable to conduct the hydrogenation reaction at pressures of from about 100 psig to about 2000 psig. The hydrogenation reaction is preferably effected in the liquid or vapor states or mixtures thereof. The total pressure will depend on the catalyst system used.

Preferably, mild temperatures and low pressures are generally considered desirable, consistent with acceptable catalyst performance and lifetime, and epsilon caprolactam precursor and epsilon caprolactam product stability. The amount of catalyst employed will be dependent on the reaction conditions employed and the amount should be sufficient to obtain the desired selectivity and degree of conversion. In general, the amount of catalyst employed should be sufficient to enable a conversion of imine to amine of at least about 5 percent, preferably at least about 20 percent, and more preferably at least about 50 percent.

It may also be advantageous to remove the water produced in an intermediate imination reaction by, for example, azeotropic distillation, extraction, absorption and other like means. Alternatively, and depending on the particular epsilon caprolactam precursor employed, the water may not be intentionally removed, but be carried through to the next stage of the reaction.

The cyclization reaction of an epsilon caprolactam precursor in which at least one functionality is a nitrogen containing functional group such as amine or imine may or may not need a catalyst, depending on the particular epsilon caprolactam precursor employed. Although it may not be absolutely necessary to employ a catalyst, it still may be desirable to do so to improve the selectivity or rate of the transformation. Other epsilon caprolactam precursors may necessitate the use of an appropriate catalyst. Since the mechanism of the cyclization reaction depends on the epsilon caprolactam precursor, the useful catalysts will be selected based upon the epsilon caprolactam precursor employed.

Catalysts and promoters useful in the cyclization stage or step include, for example, those described above useful for amination. Of course mixtures of amination and cyclization catalysts can also be employed if desired. The amount of catalyst employed will be dependent on the reaction conditions employed and the amount should be sufficient to obtain the desired selectivity and degree of conversion. In general, the amount of catalyst employed should be sufficient to enable a conversion to epsilon caprolactam of at least about 5 percent, preferably at least about 20 percent, and more preferably at least about 50 percent.

The amination and/or cyclization catalysts may be in heterogeneous form during the reaction and/or during the product separation. As an illustration, the amination and/or cyclization catalysts may be impregnated onto any solid support, such as inorganic oxides, (e.g., alumina, silica, titania, or zirconia) carbon, or ion exchange resins. The catalyst may be supported on, or intercalated inside the pores of, a zeolite or glass; the catalyst may also be dissolved in a liquid film coating the pores of said zeolite or glass. The techniques for supporting catalysts on solids, such as incipient wetness, which will be known to those skilled in the art. Descriptions of such solid catalysts may be found in for example: J. Mol. Cat. 1991, 70, 363–368; Catal. Lett. 1991, 8, 209–214; J. Organomet. Chem, 1991, 403, 221–227; Nature, 1989, 339, 454–455; J. Catal. 1985, 96, 563–573; J. Mol. Cat. 1987, 39, 243–259.

The cyclization reaction may be performed in any appropriate solvent, such as water, aromatic or aliphatic hydrocarbons or functionalized solvents such as methanol, ethanol, ketones, ethers, amides and the like, or may be carried out using the pure epsilon caprolactam precursor or the epsilon caprolactam precursor and a mixture of byproducts from the earlier stages of the reaction sequence. It is desirable that the solvent mixture employed be capable of dissolving all components of the reaction mixture, except any heterogeneous catalysts that may be employed.

A two phase system may also be used, providing adequate mixing is achieved. Such a system, however, may be used to facilitate recovery of epsilon caprolactam after the cyclization reaction by extraction, phase separation or crystallization. Cyclization reaction conditions may range from about 0° C. to about 400° C. and 20 psig to about 4500 psi for a period of about 1 minute or less to about 4 hours or longer with the longer time being used at the lower temperature, more preferably from about 50° C. to about 300° C. and from about 100 psi to about 2000 psi. The amount of catalyst used, if any, is dependent on the particular catalyst employed and the amount should be sufficient to obtain the desired selectivity and degree of conversion. It may be desirable to combine amination and cyclization steps into a single reaction zone.

While not wishing to be bound by any particular theory, the amination of an epsilon caprolactam precursor, e.g., 6-hydroxycaproic acid, and cyclization to epsilon caprolactam may proceed through a variety of intermediates. For example, in one pathway, the conversion of 6-hydroxycaproic acid may proceed through amination to first yield 6-aminocaproamide, followed by deamination/cyclization to epsilon caprolactam. In an alternate pathway, the 6-hydroxycaproic acid may first be converted to 6-hydroxycaproamide, which may then undergo dehydration/cyclization to epsilon caprolactam. The catalysts which are best able to promote the selectivity or rate of such a transformation will depend on the particular mechanism followed.

As indicated above, the substituted and unsubstituted epsilon caprolactams produced by the amination and cyclization step of this invention can be separated by conventional techniques such as distillation, extraction, precipitation, crystallization, membrane separation or other suitable means. For example, a crude reaction product can be subjected to a distillation-separation at atmospheric or reduced pressure through a packed distillation column. Reactive distillation may be useful in conducting the amination and cyclization reaction step.

Illustrative epsilon caprolactams that can be prepared by the processes of this invention include epsilon caprolactam, substituted epsilon caprolactams (e.g., alpha, beta, gamma, delta and N-substituted epsilon caprolactams) and oligomers of epsilon caprolactam. For purposes of this invention, epsilon caprolactams also include aminocaproic acid, epsilon caprolactam dimers, trimers and oligomers, and mixtures thereof with epsilon caprolactam. Illustrative of suitable substituted and unsubstituted epsilon caprolactams (including derivatives of epsilon caprolactams) include those permissible substituted and unsubstituted epsilon caprolactams which are described in Beilsteins Handbuch der Organischen Chemie, Springer Verlag KG, 4$^{th}$ Edition, the pertinent portions of which are incorporated herein by reference.

The epsilon caprolactams described herein are useful in a variety of applications, such as the manufacture of synthetic fibers (especially nylon 6), plastics, bristles, film, coatings, synthetic leather, plasticizers and paint vehicles, crosslinking agent for polyurethanes, synthesis of amino acid lysine and the like.

Dehydration and Cyclization Steps or Stages

The dehydration and cyclization processes involve converting one or more substituted or unsubstituted hydroxyamides, e.g., 6-hydroxycaproamide, and/or one or more substituted or unsubstituted epsilon caprolactam precursors to one or more substituted or unsubstituted epsilon caprolactams in one or more steps or stages. As used herein, the term "dehydration" is contemplated to include, but is not limited to, all permissible dehydration processes which in conjunction with cyclization involve converting one or more substituted or unsubstituted hydroxyamides and/or one or more substituted or unsubstituted epsilon caprolactam precursors to one or more substituted or unsubstituted epsilon caprolactams. As used herein, the term "cyclization", when used in the context of dehydration, is contemplated to include, but is not limited to, all permissible cyclization processes which in conjunction with dehydration involve converting one or more substituted or unsubstituted hydroxyamides and/or one or more substituted or unsubstituted epsilon caprolactam precursors to one or more substituted or unsubstituted epsilon caprolactams. In general, the dehydration and cyclization steps or stages comprise reacting one or more substituted or unsubstituted hydroxyamides and/or one or more substituted or unsubstituted epsilon caprolactam precursors, optionally in the presence of one or more catalysts or one or more catalysts and promoters, to produce one or more substituted or unsubstituted epsilon caprolactams.

Hydroxyamides and/or epsilon caprolactam precursors useful in the dehydration and cyclization processes are known materials and can be prepared by the oxamidation steps described above or by other conventional processes. Reaction mixtures comprising hydroxyamides and/or epsilon caprolactam precursors may be useful herein. The amounts of hydroxyamides and/or epsilon caprolactam precursors employed in the dehydration and cyclization steps are not narrowly critical and can be any amounts sufficient to produce epsilon caprolactam, preferably in high selectivities.

The dehydration and cyclization processes may be carried out in one or more steps or stages and in any permissible sequence of steps or stages. In a one step process, epsilon caprolactam is the desired product leaving the reaction zone. In a multistep or multistage process, intermediate products are the major products leaving the individual reaction zones. For example, in a two stage process, an epsilon caprolactam precursor, e.g., 6-hydroxycaproamide, may be converted directly to an amine, e.g., 6-aminocaproamide, in a first stage, and the amine may undergo deamination/cyclization to epsilon caprolactam in a second stage. Of course some overlap of these individual transformations may occur, so that in a two stage process, some cyclization may occur in the first stage.

The particular dehydration and cyclization reaction conditions are not narrowly critical and can be any effective dehydration and cyclization conditions sufficient to produce the epsilon caprolactam. The reactors may be stirred tanks, tubular reactors and the like. The exact reaction conditions will be governed by the best compromise between achieving high catalyst selectivity, activity, lifetime and ease of operability, as well as the intrinsic reactivity of the hydroxyamides and/or epsilon caprolactam precursors in question and the stability of the hydroxyamides and/or epsilon caprolactam precursors and the desired reaction product to the reaction conditions. Illustrative of certain reaction conditions that may be employed in the dehydration and/or cyclization processes are described, for example, in U.S. Pat. No. 5,495,014, supra, and U.S. Pat. No. 5,210,306, the disclosure of which is incorporated herein by reference. Products may be recovered after a particular reaction zone and purified if desired although they may be introduced to the next reaction zone without purification. Recovery and purification may be by any appropriate means, which will largely be determined by the particular epsilon caprolactam precursor employed.

The dehydration reaction can be conducted at a temperature of from about 0° C. to about 400° C. for a period of about 1 minute or less to about 4 hours or longer with the longer time being used at the lower temperature, preferably from about 50° C. to about 350° C. for about 1 minute or less to about 2 hours or longer, and more preferably at about 100° C. to about 300° C. for about 1 hour or less. The temperature should be sufficient for reaction to occur (which may vary with catalyst system) but not so high as to cause hydroxyamide decomposition or polymerization.

The dehydration reaction can be conducted over a wide range of pressures ranging from about subatmospheric to about 4500 psig. It is preferable to conduct the dehydration reaction at pressures of from about 20 psig to about 2000 psig. The dehydration reaction is preferably effected in the liquid or vapor states or mixtures thereof. The total pressure will depend on the catalyst system used.

Some of the reaction steps or stages may involve the use of a catalyst. Such catalysts are known in the art and can be homogeneous or heterogeneous. Catalysts useful in the dehydration stage or step are known materials and include, for example, Group IVB metal oxides, metallic phosphates which may or may not have a cyclic structure, metallic polyphosphates which may or may not have a condensed structure, Group VIB metal containing substances, and the like. See, for example, U.S. Pat. Nos. 5,495,014 and 5,210,306, supra. Of course mixtures of dehydration and cyclization catalysts can also be employed if desired. The amount of catalyst employed will be dependent on the dehydration and cyclization reaction conditions employed and the amount should be sufficient to obtain the desired selectivity and degree of conversion. In general, the amount of catalyst employed should be sufficient to enable a conversion to epsilon caprolactam of at least about 5 percent, preferably at least about 20 percent, and more preferably at least about 50 percent.

The dehydration process may also be conducted in the presence of a promoter. As used herein, the term "promoter", when used in the context of dehydration, means a material added to the dehydration reaction mixture to impart a promotion effect to catalytic activity, e.g., rate, product selectivity, and/or catalyst stability (mechanical or dimensional strength of the catalyst). Illustrative promoters include, for example, alkali metal hydroxide, acetate salts, Group VII metals, rare earth oxides, alkaline earth metals, and the like. The promoter may be present in the dehydration reaction mixture either alone or incorporated into the catalyst structure. The desired promoter will depend on the nature of the catalysts. The amount of promoter employed will depend upon the details of the catalyst system employed.

The cyclization reaction of an epsilon caprolactam precursor in which at least one functionality is a nitrogen containing functional group such as amine or imine may or may not need a catalyst, depending on the particular epsilon caprolactam precursor employed. Although it may not be absolutely necessary to employ a catalyst, it still may be desirable to do so to improve the selectivity or rate of the transformation. Other epsilon caprolactam precursors may necessitate the use of an appropriate catalyst. Since the mechanism of the cyclization reaction depends on the epsilon caprolactam precursor, the useful catalysts will be selected based upon the epsilon caprolactam precursor employed.

Catalysts and promoters useful in the cyclization stage or step include, for example, those described above useful for dehydration. Of course mixtures of dehydration and cyclization catalysts can also be employed if desired. The amount of catalyst employed will be dependent on the dehydration and cyclization reaction conditions employed and the amount should be sufficient to obtain the desired selectivity and degree of conversion. In general, the amount of catalyst employed should be sufficient to enable a conversion to epsilon caprolactam of at least about 5 percent, preferably at least about 20 percent, and more preferably at least about 50 percent.

As indicated above, the substituted and unsubstituted epsilon caprolactams produced by the dehydration and cyclization steps of this invention can be separated by conventional techniques such as distillation, extraction, precipitation, crystallization, membrane separation or other suitable means. For example, a crude reaction product can be subjected to a distillation-separation at atmospheric or reduced pressure through a packed distillation column. Reactive distillation may be useful in conducting the dehydration and cyclization reaction steps. Illustrative epsilon caprolactams that can be prepared by the processes of this invention are described above.

Deamination and Cyclization Steps or Stages

The deamination and cyclization processes involve converting one or more substituted or unsubstituted aminoamides, e.g., 6-aminocaproamide, and/or one or more other substituted or unsubstituted epsilon caprolactam precursors to one or more substituted or unsubstituted epsilon caprolactams in one or more steps or stages. As used herein, the term "deamination" is contemplated to include, but is not limited to, all permissible deamination processes which in conjunction with cyclization involve converting one or more substituted or unsubstituted aminoamides and/or one or more other substituted or unsubstituted epsilon caprolactam precursors to one or more substituted or unsubstituted epsilon caprolactams. As used herein, the term "cyclization", when used in the context of deamination, is contemplated to include, but is not limited to, all permissible cyclization processes which in conjunction with deamination involve converting one or more substituted or unsubstituted aminoamides and/or one or more other substituted or unsubstituted epsilon caprolactam precursors to one or more substituted or unsubstituted epsilon caprolactams. In general, the deamination and cyclization steps or stages comprise reacting one or more substituted or unsubstituted aminoamides and/or one or more other substituted or unsubstituted epsilon caprolactam precursors, optionally in the presence of one or more catalysts or one or more catalysts and promoters, to produce one or more substituted or unsubstituted epsilon caprolactams.

Aminoamides and/or other epsilon caprolactam precursors useful in the deamination and cyclization processes are known materials and can be prepared by the oxamidation steps described above or by other conventional processes. Illustrative substituted and unsubstituted aminoamide intermediates that can be prepared by the oxamidation stage or step of this invention include one or more of the following: aminoamides such as 6-aminocaproamide, 5-amino-2-methylvaleramide, 4-amino-2-ethylbutyramide, including mixtures comprising one or more of the above aminoamides.

Reaction mixtures comprising aminoamides and/or other epsilon caprolactam precursors may be useful herein. The amounts of aminoamides and/or other epsilon caprolactam precursors employed in the deamination and cyclization steps are not narrowly critical and can be any amounts sufficient to produce epsilon caprolactam, preferably in high selectivities.

The deamination and cyclization processes may be carried out in one or more steps or stages and in any permissible sequence of steps or stages. In a one step process, epsilon caprolactam is the desired product leaving the reaction zone. In a multistep or multistage process, intermediate products are the major products leaving the individual reaction zones. For example, in a two stage process, an epsilon caprolactam precursor, e.g., 6-aminocaproamide, may be converted directly to an aminoacid, e.g., 6-aminocaproic acid, in a first stage, and the aminoacid may be cyclized to epsilon caprolactam in a second stage. Of course some overlap of these individual transformations may occur, so that in a two stage process, some cyclization may occur in the first stage.

The particular deamination and cyclization reaction conditions are not narrowly critical and can be any effective deamination and cyclization conditions sufficient to produce the epsilon caprolactam. The reactors may be stirred tanks, tubular reactors and the like. The exact reaction conditions will be governed by the best compromise between achieving high catalyst selectivity, activity, lifetime and ease of operability, as well as the intrinsic reactivity of the aminoamides and/or other epsilon caprolactam precursors in question and the stability of the aminoamides and/or other epsilon caprolactam precursors and the desired reaction product to the reaction conditions. Illustrative of certain reaction conditions that may be employed in the deamination and/or cyclization processes are described, for example, in U.S. Pat. Nos. 5,495,014 and 4,730,041, supra. Products may be recovered after a particular reaction zone and purified if desired although they may be introduced to the next reaction zone without purification. Recovery and purification may be by any appropriate means, which will largely be determined by the particular epsilon caprolactam precursor employed.

The deamination reaction can be conducted at a temperature of from about 0° C. to about 400° C. for a period of about 1 minute or less to about 4 hours or longer with the longer time being used at the lower temperature, preferably from about 50° C. to about 350° C. for about 1 minute or less to about 2 hours or longer, and more preferably at about 100° C. to about 300° C. for about 1 hour or less. The temperature should be sufficient for reaction to occur (which may vary with catalyst system) but not so high as to cause aminoamide decomposition or polymerization.

The deamination reaction can be conducted over a wide range of pressures ranging from about subatmospheric to about 4500 psig. It is preferable to conduct the deamination reaction at pressures of from about 20 psig to about 2000 psig. The deamination reaction is preferably effected in the liquid or vapor states or mixtures thereof. The total pressure will depend on the catalyst system used.

Some of the reaction steps or stages may involve the use of a catalyst. Such catalysts are known in the art and can be homogeneous or heterogeneous. Catalysts useful in the deamination stage or step are those described above useful in amination. See, for example, in U.S. Pat. Nos. 5,495,014, 5,646,277, 4,123,462, 5,750,790, 5,891,820 and 4,730,041, supra. Of course mixtures of deamination and cyclization catalysts can also be employed if desired. The amount of catalyst employed will be dependent on the deamination and cyclization reaction conditions employed and the amount should be sufficient to obtain the desired selectivity and degree of conversion. In general, the amount of catalyst employed should be sufficient to enable a conversion to epsilon caprolactam of at least about 5 percent, preferably at least about 20 percent, and more preferably at least about 50 percent.

The deamination process may also be conducted in the presence of a promoter. As used herein, the term "promoter", when used in the context of deamination, means a material added to the deamination reaction mixture to impart a promotion effect to catalytic activity, e.g., rate, product selectivity, and/or catalyst stability (mechanical or dimensional strength of the catalyst). Illustrative promoters include, for example, alkali metal hydroxide, acetate salts, Group VII metals, rare earth oxides, alkaline earth metals, and the like. The promoter may be present in the deamination reaction mixture either alone or incorporated into the catalyst structure. The desired promoter will depend on the nature of the catalysts. The amount of promoter employed will depend upon the details of the catalyst system employed.

The cyclization reaction of an epsilon caprolactam precursor in which at least one functionality is a nitrogen containing functional group such as amine or imine may or may not need a catalyst, depending on the particular epsilon caprolactam precursor employed. Although it may not be absolutely necessary to employ a catalyst, it still may be desirable to do so to improve the selectivity or rate of the transformation. Other epsilon caprolactam precursors may necessitate the use of an appropriate catalyst. Since the mechanism of the cyclization reaction depends on the epsilon caprolactam precursor, the useful catalysts will be selected based upon the epsilon caprolactam precursor employed.

Catalysts and promoters useful in the cyclization stage or step include, for example, those described above useful for deamination. Of course mixtures of deamination and cyclization catalysts can also be employed if desired. The amount of catalyst employed will be dependent on the deamination and cyclization reaction conditions employed and the amount should be sufficient to obtain the desired selectivity and degree of conversion. In general, the amount of catalyst employed should be sufficient to enable a conversion to epsilon caprolactam of at least about 5 percent, preferably at least about 20 percent, and more preferably at least about 50 percent.

As indicated above, the substituted and unsubstituted epsilon caprolactams produced by the deamination and cyclization steps of this invention can be separated by conventional techniques such as distillation, extraction, precipitation, crystallization, membrane separation or other suitable means. For example, a crude reaction product can be subjected to a distillation-separation at atmospheric or reduced pressure through a packed distillation column. Reactive distillation may be useful in conducting the deamination and cyclization reaction steps. Illustrative epsilon caprolactams that can be prepared by the processes of this invention are described above.

Other substituted and unsubstituted epsilon caprolactam precursors produced by the processes of this invention can undergo further reaction(s) to afford epsilon caprolactam or desired derivatives thereof Such permissible derivatization reactions can be carried out in accordance with conventional procedures known in the art. Illustrative derivatization reactions include, for example, hydrogenation, esterification, polymerization, copolymerization, amination, alkylation, dehydrogenation, reduction, acylation, condensation, oxidation, silylation and the like, including permissible combinations thereof This invention is not intended to be limited in any manner by the permissible derivatization reactions or permissible derivatives of substituted and unsubstituted epsilon caprolactam precursors.

The processes of this invention can be operated over a wide range of reaction rates (m/L/h=moles of product/liter of reaction solution/hour or m/kg cat/h=moles of product/kilogram of catalyst/hour). Typically, when employing a homogeneous catalyst, the reaction rates are at least 0.01 m/L/h or higher, preferably at least 0.1 m/L/h or higher, and more preferably at least 0.5 m/L/h or higher. When employing a heterogeneous catalyst, the reaction rates are at least 0.1 m/kg cat/h or higher, preferably at least 1.0 m/kg cat/h or higher, and more preferably at least 5.0 m/kg cat/h or higher. Higher reaction rates are generally preferred from an economic standpoint, e.g., smaller reactor size, etc.

The processes of this invention may be carried out using, for example, a fixed bed reactor, a fluid bed reactor, a continuous stirred tank reactor (CSTR) or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The processes of this invention may be conducted in one or more steps or stages. The exact number of reaction steps or stages will be governed by the best compromise between achieving high catalyst selectivity, activity, lifetime and ease of operability, as well as the intrinsic reactivity of the starting materials in question and the stability of the starting materials and the desired reaction product to the reaction conditions.

The substituted and unsubstituted epsilon caprolactams produced by the processes of this invention can undergo further reaction(s) to afford desired derivatives thereof. Such permissible derivatization reactions can be carried out in accordance with conventional procedures known in the art. Illustrative derivatization reactions include, for example, hydrogenation, esterification, polymerization, copolymerization, amination, alkylation, dehydrogenation, reduction, acylation, condensation, oxidation, silylation and the like, including permissible combinations thereof This invention is not intended to be limited in any manner by the permissible derivatization reactions or permissible derivatives of substituted and unsubstituted epsilon caprolactams.

In an embodiment of this invention, after optional purification of epsilon caprolactam, nylon 6 polymer is produced from epsilon caprolactam by continuous polymerization or batch polymerization processes. In both reaction processes for forming nylon 6, polymerization occurs according to the following reactions: epsilon caprolactam (mol. wt. 113)+ $H_2O \rightarrow$ aminocaproic acid (mol. wt. 131) $\rightarrow$ nylon 6 (mol. wt. 14,000–20,000)+$H_2O$. Suitable reactors and polymerization reaction conditions for nylon 6 are known in the art.

In a continuous polymerization process, high-purity, molten caprolactam is taken from storage and pumped to a tank where controlled amounts of water (the initiator), recovered monomer and oligomers, a chain terminator (e.g., acetic acid) and other additives such as heat and light stabilizers are mixed together. The caprolactam is maintained in a nitrogen environment both in the holding tanks and throughout the polymerization process. The melted caprolactam solution is then filtered and metered into the reaction vessel where polymerization occurs.

The reaction vessel, which is generally eight to ten meters high and mounted vertically, is usually equipped with several independent heating jackets that control the temperature of the reactants as they pass down the tube. Polymerization occurs at atmospheric pressure as the reactants pass slowly through the tube and as the temperature increases to about 275° C. After 20–24 hours, the nylon 6 polymer reaches equilibrium and is extruded as strands into a water quenching bath; the strands are then cut into chips that are also stored under nitrogen.

In a batch polymerization process, high-purity melted epsilon caprolactam (about 80° C.) is pumped into an autoclave. Water, which serves as an initiator, is added to form up to a 5% solution and the temperature of the solution is increased to 220–270° C. The pressure increases with increasing temperature, and polymerization occurs.

Addition of a polymer chain terminator such as acetic acid controls molecular weight and thus the viscosity of the resin. After several hours, when the caprolactam conversion to polymer has reached equilibrium, water is removed by reducing the pressure to achieve a vacuum. The removal of water is necessary to achieve the desired molecular weight. After the water removal, the polymerization mixture may be held until the molecular weight reaches equilibrium. Finally, the molten resin is extruded as strands into a water quenching bath: the strands are then cut into chips.

As used herein, the term "substituted or unsubstituted epsilon caprolactam precursors" is contemplated to include, but is not limited to, one or more iminoacids such as iminocaproic acid, aminoacids such as aminocaproic acid, hydroxyacids such as hydroxycaproic acid, diacids such as adipic acid, diamides such as adipamide, aldehyde acids such as formylvaleric acid, caprolactam, caprolactone, caprolactone oligomers, esters of hydroxyacids such as esters of 6-hydroxycaproic acid, imines such as hexamethyleneimine, amines such as hexamethylenediamine, hemiaminals, imides, hydroxyamides, formylamides, aminoamides, amides or amines derived from hydroxyacids, and the corresponding dimers, trimers and oligomers. This invention is not intended to be limited in any manner by the permissible epsilon caprolactam precursors.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

For purposes of this invention, the chemical elements are identified in accordance with the Periodic Table of the Elements reproduced in "Basic Inorganic Chemistry" by F. Albert Cotton, Geoffrey Wilkinson and Paul L. Gaus, published by John Wiley and Sons, Inc., 3rd Edition, 1995.

Certain of the following examples are provided to further illustrate this invention.

COMPARATIVE EXAMPLE A

Into a 100 milliliter Parr autoclave reactor was charged 5.09 grams of nickel, rhenium, boron on silica catalyst powder (made by crushing catalyst pellets in a mortar and pestle) as described in Example 6 of U.S. Pat. No. 4,123,462. The reactor was purged with nitrogen. While under 15 psi $N_2$, 15 psi $H_2$ pressure was added and the reactor was heated to 225° C. The pressure began to decrease slowly at about 185° C. $H_2$ pressure was increased to 100 psi and heating was continue at 225° C. for 5 hours. The reactor was cooled and allowed to sit under 60 psi $H_2$ overnight. The reactor was purged of excess $H_2$. A solution consisting of 1.08 grams of 6-hydroxyhexanal in 10 milliliters of water, and 20 milliliters of concentrated $NH_4OH$, was charged to the reactor and the reactor was heated to 225° C. while stirring. After 3 hours at 225° C. the reactor was cooled and sampled for gas chromatographic analysis. Gas chromatographic analysis showed about 32% selectivity to epsilon caprolactam.

COMPARATIVE EXAMPLE B

To a 300 milliliter Parr reactor was charged 0.5143 grams of a powdered nickel, rhenium, boron catalyst prepared as described in Example 6 of U.S. Pat. No. 4,123,462. The catalyst was activated in 21.4 grams water for 1 hour at 200° C. under 400 psig hydrogen. The reactor was cooled, and a solution of 2.12 grams of 6-hydroxyhexanal, 10.61 grams water and 2.91 grams of tetraglyme, as internal standard, was charged to the reactor along with 50 milliliters of 28–31% $NH_3$ in water. The reactor was heated to 120° C. under 200 psig hydrogen. Product yields were determined using gas chromatographic analysis of samples taken over time and were based on the amount of 6-hydroxyhexanal charged. After 2 hours of reaction at 120° C., Sample A was taken and analyzed by gas chromatography. The reactor was then vented slowly to ambient pressure to vent hydrogen and ammonia. The reactor was re-pressurized with 20 psig hydrogen and heated to 220° C. Analysis of samples taken after continued reaction for one hour, Sample B, and 2 hours, Sample C, gave the results shown in the table below.

TABLE

| Time | Epsilon Caprolactam | Hexamethylene-imine | 6-Aminohexanol |
|---|---|---|---|
| Sample A | 0.0 | 0.3 | 90.6 |
| Sample B | 1.1 | 19.5 | 60.6 |
| Sample C | 6.4 | 12.8 | 0.0 |

COMPARATIVE EXAMPLE C

To a 300 milliliter Parr reactor was charged 0.5 grams of Raney Nickel catalyst. The reactor was sealed, placed under an atmosphere of nitrogen and a solution of 2.05 grams of 6-hydroxyhexanal, 3.08 grams tetraglyme, as internal standard, and 51.05 grams water was charged. The reactor was pressurized to 515 psig with hydrogen and heated to 120° C. for 2 hours. A sample taken after that time was analyzed by gas chromatography and indicated a 87 percent yield of 1,6-hexanediol. The reactor was then cooled, vented of hydrogen pressure and 50 milliliters of 28% $NH_3$ in water was added. The reactor was pressurized with 50 psig hydrogen and heated to 225° C. Gas chromatographic analysis of the reaction mixture after 75 minutes showed yields of 52% hexamethyleneimine, 12% hexamethylenediamine, and 4% epsilon caprolactam.

EXAMPLE 1

5.20 Grams (45 mmols) of 6-hydroxyhexanal was charged to a 100 milliliter Schlenk flask and dissolved in 45 milliliters of deionized water by heating to 85–95° C. in a water bath. The resulting solution was charged to a 100 milliliter Parr autoclave and placed under 600 psi air. 1 Milliliter of a sodium persulfate solution (0.520 grams of $Na_2S_2O_8$/20milliliters of water) was added via a Gilson pump. The reactor was then heated to 80° C. and a 1800 psi air purge was established. Additional quantities of sodium persulfate were added as follows: at 1 hour (1 milliliter), at 1.5 hours (1 milliliter), and at 2 hours (0.5 milliliters). After 1.5 hours, the reaction conversion was 85% and selectivity to 6-hydroxycaproic acid was 98%. After 2.5 hours, reaction conversion was 99% and selectivity to 6-hydroxycaproic acid was 90%.

EXAMPLE 2

5.26 Grams (45 mmols) of 6-hydroxyhexanal was charged to a 100 milliliter Schlenk flask and dissolved in 10 milliliters of deionized water by heating to 85–95° C. in a water bath. The resulting solution was charged to the Parr autoclave containing 0.484 grams of $Na_2S_2O_8$ and 35 milliliters of $NH_4OH$. The reactor was placed under 400 psi air, heated to 80° C. and a 500 psi air purge was established. The reaction was allowed to proceed for 3 hours. At that time, reaction conversion was virtually complete and 6-hydroxycaproamide was formed in 40% yield.

EXAMPLE 3

5.28 Grams (45 mmols) of 6-hydroxyhexanal was charged to a 100 milliliter Schlenk flask and dissolved in 45 milliliters of deionized water by heating to 85–95° C. in a water bath. The resulting solution was charged to the Parr autoclave, placed under 1500 psi $O_2$ and heated to 120° C. Samples were taken every 30 minutes throughout the reaction. After 1.5 hours, reaction conversion was 92% and 6-hydroxycaproic acid was formed in 92% selectivity.

EXAMPLE 4

5.27 Grams (45 mmols) of 6-hydroxyhexanal was charged to a 100 milliliter Schlenk flask and dissolved in 45 milliliters of deionized water by heating to 85–95° C. in a water bath. The resulting solution was charged to the Parr autoclave, placed under 1500 psi air and heated to 120° C. Samples were taken every 30 minutes throughout the reaction. After 1.5 hours, reaction conversion was 89% and 6-hydroxycaproic acid was formed in 91% selectivity.

EXAMPLE 5

5.28 Grams (45 mmols) of 6-hydroxyhexanal was charged to a 100 milliliter Schlenk flask and dissolved in 10 milliliters of deionized water by heating to 85–95° C. in a water bath. The resulting solution was charged to the Parr autoclave containing 35 milliliters of $NH_4OH$. The reactor was placed under 400 psi air, heated to 80° C. and a 500 psi air purge was established. Reaction was allowed to proceed for 3 hours. At that time, reaction conversion was virtually complete and 6-hydroxycaproamide was formed in 35% yield.

EXAMPLE 6

A solution was prepared from 44.2 grams of 7% 6-hydroxyhexanal in water and 2.5 grams of tetraglyme (internal standard). Three Fisher-Porter tubes (3 ounces each) were charged as follows: tube 1 contained no catalyst, tube 2 contained 0.0493 grams of 5% Pt/C and tube 3 contained 0.0451 grams of 5% Pd/C. Each tube was then charged with 15 milliliters of the 6-hydroxyhexanal/water solution and the tubes heated in an oil bath having an oil temperature of 100° C. Air was sparged through the solutions at 50 milliliters per minute with the reaction pressures maintained at 60 psig via back pressure regulators. The internal temperature within one of the tubes was monitored and ranged from an early value of 97° C., and settled at 73° C. After about 8 hours of reaction, gas chromatographic analysis of the solutions gave the following results:

|  | Tube 1 | Tube 2 | Tube 3 |
| --- | --- | --- | --- |
| 6-Hydroxycaproic Acid Yield, % | 71 | 75 | 61 |
| 6-Hydroxycaproic Acid/Epsilon Caprolactone Yield, % | 75 | 81 | 65 |
| 6-Hydroxyhexanal Conversion, % | 84 | 90 | 81 |

EXAMPLE 7

A solution of 10.32 grams of epsilon caprolactone, 2.99 grams of tetraglyme, 12.38 grams of water and 2.1 grams of Raney 3110 nickel catalyst was charged to a 300 milliliter Parr reactor. The reactor was sealed, placed under an atmosphere of nitrogen and 87.9 grams of 28% ammonia in water was added. The reactor was pressurized with 60 psig hydrogen and heated to 220° C. After 5 hours of reaction, gas chromatographic analysis of the reaction mixture showed the following as normalized percents: epsilon caprolactam (74%), aminocaproic acid (2%), hydroxycaproamide (14%) and an additional component (9%), possibly aminocaproamide.

EXAMPLE 8

To a catalyst basket in a 300 milliliter Parr reactor was charged 5.044 grams of a nickel, rhenium, boron catalyst prepared as described in Example 6 of U.S. Pat. No. 4,123,462. The catalyst was activated in 50 milliliters of water for 1 hour at 200° C. under 533 psig hydrogen. The reactor was cooled, vented, and the water discharged. 50 Milliliters of 17% $NH_3$ in water was charged to the reactor and the reactor was heated to 235° C. under 220 psig of 3% hydrogen in nitrogen. A flow of 40 milliliters per minute of 3% hydrogen in nitrogen was maintained through the reactor using a Brooks Mass Flow Meter at a reactor pressure of 725 psig. A solution of 5.00 grams of 6-aminohexanol, 20 grams water and 2.04 grams of tetreglyme as internal standard was prepared and charged to a stainless steel pressure cylinder connected to a metering pump. The 6-aminohexanol in water solution was fed to the reactor at a rate of 1.0 milliliter per minute. The yields of products, i.e., epsilon caprolactam, hexamethyleneimine, and hexamethylenediamine, were determined using gas chromatographic analysis of samples taken over time and were based on the amount of 6-aminohexanol charged. From the time when the 6-aminohexanol feed was completed, the yields of epsilon caprolactam, hexamethyleneimine, and hexamethylenediamine with are shown in the table below.

TABLE

| Time | Epsilon Caprolactam | Hexamethylene-imine | Hexamethylene-diamine |
| --- | --- | --- | --- |
| 0 | 2.3 | 16.0 | 5.3 |
| 1 | 4.9 | 21.7 | 6.4 |
| 2 | 11.8 | 19.2 | 4.5 |
| 3 | 16.3 | 12.1 | 2.2 |
| 4 | 17.6 | 8.8 | 0.0 |

EXAMPLE 9

To a catalyst basket in a 300 milliliter Parr reactor was charged 5.01 grams of a nickel, rhenium, boron catalyst prepared as described in Example 6 of U.S. Pat. No. 4,123,462. The catalyst was activated in 50 milliliters of water for 1 hour at 200° C. under 542 psig hydrogen. The reactor was cooled, the water discharged and the hydrogen pressure vented. 60 Milliliters of 28% $NH_3$ in water was charged to the reactor. A solution was prepared from 5.07 grams of 87% hydroxycaproic acid, 10% hydroxycaproic acid dimer and 1% percent epsilon caprolactone, 20.05 grams of water and 4.02 grams of tetraglyme as internal standard. The solution was charged to the reactor, and the reactor was pressurized to 400 psig of 3% hydrogen in nitrogen then heated to 225° C. A flow of 40 milliliters per minute of 3% hydrogen in nitrogen was maintained through the reactor using a Brooks Mass Flow Meter at a reactor pressure of 570 psig. After 3 hours of reaction at 224° C., a sample of the reaction mixture was analyzed by gas chromatography indicating a 68.6% yield of epsilon caprolactam.

EXAMPLE 10

To a catalyst basket in a 300 milliliter Parr reactor was charged 5.39 grams of a nickel, rhenium, boron catalyst prepared as described in Example 6 of U.S. Pat. No. 4,123,462. The catalyst was activated in 50 milliliters of water for 1 hour at 200° C. under 540 psig hydrogen. The reactor was cooled, the water discharged and the hydrogen pressure vented. The reactor was then charged with a solution of 11.22 grams of epsilon caprolactone, 14.08 grams water and 4.87 grams of tetraglyme as internal standard. 100 Milliliters of 28% $NH_3$ in water was added and the reactor was heated to 225° C. under 400 psig of 3% hydrogen in nitrogen. A flow of 40 milliliters per minute of 3% hydrogen in nitrogen was maintained through the reactor using a Brooks Mass Flow Meter at a reactor pressure of 570 psig. After 4 hours of reaction at 224° C., a sample of the reaction mixture was analyzed by gas chromatography indicating a 59.2% yield of epsilon caprolactam.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for producing one or more substituted or unsubstituted epsilon caprolactams which comprises (a) converting one or more substituted or unsubstituted 6-hydroxyaldehydes, optionally in the presence of a catalyst or a catalyst and promoter, to one or more substituted or unsubstituted 6-hydroxyamides and/or one or more substituted or unsubstituted epsilon caprolactam precursors, and (b) converting said one or more substituted or unsubstituted 6-hydroxyamides and/or said one or more substituted or unsubstituted epsilon caprolactam precursors, optionally in the presence of a catalyst or a catalyst and promoter, to said one or more substituted or unsubstituted epsilon caprolactams; wherein the amount of byproducts resulting from reduction and/or reductive amination of said one or more substituted or unsubstituted 6-hydroxyaldehydes is no greater than about 10 weight percent of the total of said one or more substituted or unsubstituted 6-hydroxyamides and/or one or more substituted or unsubstituted epsilon caprolactam precursors.

2. The process of claim 1 which further comprises converting said one or more substituted or unsubstituted hydroxyaldehydes, optionally in the presence of a catalyst or a catalyst and promoter, to one or more substituted or unsubstituted hydroxyamides and/or one or more substituted or unsubstituted epsilon caprolactam precursors, optionally in the presence of an initiator.

3. A process for producing one or more substituted or unsubstituted epsilon caprolactams which comprises (a) converting one or more substituted or unsubstituted 6-hydroxyaldehydes, optionally in the presence of a catalyst or a catalyst and promoter, to one or more substituted or unsubstituted 6-hydroxyacids and/or one or more substituted or unsubstituted epsilon caprolactam precursors, and (b) converting said one or more substituted or unsubstituted 6-hydroxyacids and/or said one or more substituted or unsubstituted epsilon caprolactam precursors, optionally in the presence of a catalyst or a catalyst and promoter, to said one or more substituted or unsubstituted epsilon caprolactams; wherein the amount of byproducts resulting from reduction and/or reductive amination of said one or more substituted or unsubstituted 6-hydroxyaldehydes is no greater than about 10 weight percent of the total of said one or more substituted or unsubstituted 6-hydroxyacids and/or one or more substituted or unsubstituted epsilon caprolactam precursors.

4. The process of claim 3 which further comprises converting said one or more substituted or unsubstituted hydroxyaldehydes, optionally in the presence of a catalyst or a catalyst and promoter, to one or more substituted or unsubstituted hydroxyacids and/or one or more substituted or unsubstituted epsilon caprolactam precursors, optionally in the presence of an initiator.

5. A process for producing one or more substituted or unsubstituted epsilon caprolactams which comprises (a) subjecting one or more substituted or unsubstituted 6-hydroxyaldehydes to oxamidation, optionally in the presence of an oxamidation catalyst or an oxamidation catalyst and promoter, to produce one or more substituted or unsubstituted 6-hydroxyamides and/or one or more substituted or unsubstituted epsilon caprolactam precursors, and (b) subjecting said one or more substituted or unsubstituted 6-hydroxyamides and/or said one or more substituted or unsubstituted epsilon caprolactam precursors to dehydration, optionally in the presence of a dehydration catalyst or a dehydration catalyst and promoter, and cyclization, optionally in the presence of a cyclization catalyst or a cyclization catalyst and promoter, to produce said one or more substituted or unsubstituted epsilon caprolactams; wherein the amount of byproducts resulting from reduction and/or reductive amination of said one or more substituted or unsubstituted 6-hydroxyaldehydes is no greater than about 10 weight percent of the total of said one or more substituted or unsubstituted 6-hydroxyamides and/or one or more substituted or unsubstituted epsilon caprolactam precursors.

6. A process for producing one or more substituted or unsubstituted epsilon caprolactams which comprises (a) subjecting one or more substituted or unsubstituted 6-hydroxyaldehydes to oxidation, optionally in the presence of an oxidation catalyst or an oxidation catalyst and promoter, to produce one or more substituted or unsubstituted 6-hydroxyacids and/or one or more substituted or unsubstituted epsilon caprolactam precursors, and (b) subjecting said one or more substituted or unsubstituted 6-hydroxyacids and/or said one or more substituted or unsubstituted epsilon caprolactam precursors to amination, optionally in the presence of an amination catalyst or an amination catalyst and promoter, and cyclization, optionally in the presence of a cyclization catalyst or a cyclization catalyst and promoter, to produce said one or more substituted or unsubstituted epsilon caprolactams; wherein the amount of byproducts resulting from reduction and/or reductive amination of said one or more substituted or unsubstituted 6-hydroxyaldehydes is no greater than about 10 weight percent of the total of said one or more substituted or unsubstituted 6-hydroxyacids and/or one or more substituted or unsubstituted epsilon caprolactam precursors.

7. The process of claim 5 which further comprises subjecting said one or more substituted or unsubstituted epsilon caprolactam precursors comprising aminoamides to deamination, optionally in the presence of a deamination catalyst or a deamination catalyst and promoter., and cyclization, optionally in the presence of a cyclization catalyst or a cyclization catalyst and promoter, to produce said one or more substituted or unsubstituted epsilon caprolactams.

8. A process for producing a batchwise or continuously generated reaction mixture comprising:
   (1) one or more substituted or unsubstituted epsilon caprolactams;
   (2) optionally one or more substituted or unsubstituted 6-hydroxyamides;

(3) optionally one or more substituted or unsubstituted epsilon caprolactam precursors; and (4) one or more substituted or unsubstituted 6-hydroxyaldehydes;

wherein the weight ratio of component (1) to the sum of components (2), (3), and (4) is greater than about 0.1, and the weight ratio of component (4) to the sum of components (1), (2), and (3) is about 0 to about 100;

which process comprises (a) subjecting one or more substituted or unsubstituted 6-hydroxyaldehydes to oxamidation, optionally in the presence of an oxamidation catalyst or an oxamidation catalyst and promoter, to produce one or more substituted or unsubstituted 6-hydroxyamides and/or one or more substituted or unsubstituted epsilon caprolactams precursors, and (b) subjecting said one or more substituted or unsubstituted epsilon caprolactam precursors to dehydration, optionally in the presence of a dehydration catalyst or a dehydration catalyst and promoter, and cyclization, optionally in the presence of a cyclization catalyst or a cyclization catalyst and promoter, to produce said batchwise or continuously generated reaction mixture; wherein the amount of byproducts resulting from reduction and/or reductive amination of said one or more substituted or unsubstituted 6-hydroxyaldehydes is no greater than about 10 weight percent of the total of said one or more substituted or unsubstituted 6-hydroxyamides and/or one or more substituted or unsubstituted epsilon caprolactam precursors.

9. A process for producing a batchwise or continuously generated reaction mixture comprising:

(1) one or more substituted or unsubstituted epsilon caprolactams;

(2) optionally one or more substituted or unsubstituted 6-hydroxyacids;

(3) optionally one or more substituted or unsubstituted epsilon caprolactam precursors; and (4) one or more substituted or unsubstituted 6-hydroxyaldehydes;

wherein the weight ratio of component (1) to the sum of components (2), (3), and (4) is greater than about 0.1, and the weight ratio of component (4) to the sum of components (1), (2), and (3) is about 0 to about 100;

which process comprises (a) subjecting one or more substituted or unsubstituted 6-hydroxyaldehydes to oxidation, optionally in the presence of an oxidation catalyst or an oxidation catalyst and promoter, to produce one or more substituted or unsubstituted 6-hydroxyacids and/or said one or more substituted or unsubstituted epsilon caprolactams precursors, and (b) subjecting said one or more substituted or unsubstituted 6-hydroxyacids and/or said one or more substituted or unsubstituted epsilon caprolactam precursors to amination, optionally in the presence of an amination catalyst or an amination catalyst and promoter, and cyclization, optionally in the presence of a cyclization catalyst or a cyclization catalyst and promoter, to produce said batchwise or continuously generated reaction mixture; wherein the amount of byproducts resulting from reduction and/or reductive amination of said one or more substituted or unsubstituted 6-hydroxyaldehydes is no greater than about 10 weight percent of the total of said one or more substituted or unsubstituted 6-hydroxyacids and/or one or more substituted or unsubstituted epsilon caprolactam precursors.

10. The process of claim 8 which further comprises subjecting said one or more substituted or unsubstituted epsilon caprolactam precursors comprising aminoamides to deamination, optionally in the presence of a deamination catalyst or a deamination catalyst and promoter, and cyclization, optionally in the presence of a cyclization catalyst or a cyclization catalyst and promoter, to produce said one or more substituted or unsubstituted epsilon caprolactams.

11. A process for producing a reaction mixture comprising one or more substituted or unsubstituted epsilon caprolactams which process comprises (a) subjecting one or more substituted or unsubstituted 6-hydroxyaldehydes to oxamidation, optionally in the presence of an oxamidation catalyst or an oxamidation catalyst and promoter, to produce one or more substituted or unsubstituted 6-hydroxyamides and/or one or more substituted or unsubstituted epsilon caprolactam precursors, and (b) subjecting said one or more substituted or unsubstituted 6-hydroxyamides and/or said one or more substituted or unsubstituted epsilon caprolactam precursors to dehydration, optionally in the presence of a dehydration catalyst or a dehydration catalyst and promoter, and cyclization, optionally in the presence of a cyclization catalyst or a cyclization catalyst and promoter, to produce said reaction mixture comprising one or more substituted or unsubstituted epsilon caprolactams; wherein the amount of byproducts resulting from reduction and/or reductive amination of said one or more substituted or unsubstituted 6-hydroxyaldehydes is no greater than about 10 weight percent of the total of said one or more substituted or unsubstituted 6-hydroxyamides and/or one or more substituted or unsubstituted epsilon caprolactam precursors.

12. A process for producing a reaction mixture comprising one or more substituted or unsubstituted epsilon caprolactams which process comprises (a) subjecting one or more substituted or unsubstituted 6-hydroxyaldehydes to oxidation, optionally in the presence of an oxidation catalyst or an oxidation catalyst and promoter, to produce one or more substituted or unsubstituted 6-hydroxyacids and/or one or more substituted or unsubstituted epsilon caprolactam precursors, and (b) subjecting said one or more substituted or unsubstituted 6-hydroxyacids and/or said one or more substituted or unsubstituted epsilon caprolactam precursors to amination, optionally in the presence of an amination catalyst or an amination catalyst and promoter, and cyclization, optionally in the presence of a cyclization catalyst and a cyclization catalyst and promoter, to produce said reaction mixture comprising one or more substituted or unsubstituted epsilon caprolactams; wherein the amount of byproducts resulting from reduction and/or reductive amination of said one or more substituted or unsubstituted 6-hydroxyaldehydes is no greater than about 10 weight percent of the total of said one or more substituted or unsubstituted 6-hydroxyacids and/or one or more substituted or unsubstituted epsilon caprolactam precursors.

13. The process of claim 11 which further comprises subjecting said one or more substituted or unsubstituted epsilon caprolactam precursors comprising aminoamides to deamination, optionally in the presence of a deamination catalyst or a deamination catalyst and promoter, and cyclization, optionally in the presence of a cyclization catalyst or a cyclization catalyst and promoter, to produce said one or more substituted or unsubstituted epsilon caprolactams.

14. A batchwise or continuously generated reaction mixture comprising:

(1) one or more substituted or unsubstituted epsilon caprolactams;

(2) optionally one or more substituted or unsubstituted 6-hydroxyamides;

(3) optionally one or more substituted or unsubstituted epsilon caprolactam precursors; and (4) one or more substituted or unsubstituted 6-hydroxyaldehydes;

wherein the weight ratio of component (1) to the sum of the components (2), (3), and (4) is greater than about 0. 1, and the weight ratio of component (4) to the sum of components (1), (2), and (3) is about 0 to about 100.

15. A batchwise or continuously generated reaction mixture comprising:

(1) one or more substituted or unsubstituted epsilon caprolactams;

(2) optionally one or more substituted or unsubstituted 6-hydroxyacids;

(3) optionally one or more substituted or unsubstituted epsilon caprolactam precursors; and (4) one or more substituted or unsubstituted 6-hydroxyaldehydes;

wherein the weight ratio of component (1) to the sum of the components (2), (3), and (4) is greater than about 0. 1, and the weight ratio of component (4) to the sum of components (1), (2), and (3) is about 0 to about 100.

16. A reaction mixture comprising one or more substituted or unsubstituted epsilon caprolactams in which said reaction mixture is prepared by a process which comprises: (a) subjecting one or more substituted or unsubstituted 6-hydroxyaldehydes to oxamidation, optionally in the presence of an oxamidation catalyst or an oxamidation catalyst and promoter, to produce one or more substituted or unsubstituted 6-hydroxyamides and/or one or more substituted or unsubstituted epsilon caprolactam precursors, and (b) subjecting said one or more substituted or unsubstituted 6-hydroxyamides and/or said one or more substituted or unsubstituted epsilon caprolactam precursors to dehydration, optionally in the presence of a dehydration catalyst or a dehydration catalyst and promoter, and cyclization, optionally in the presence of a cyclization catalyst or a cyclization catalyst and promoter, to produce said reaction mixture comprising one or more substituted or unsubstituted epsilon caprolactams; wherein the amount of byproducts resulting from reduction and/or reductive amination of said one or more substituted or unsubstituted 6-hydroxyaldehydes is no greater than about 10 weight percent of the total of said one or more substituted or unsubstituted 6-hydroxyamides and/or one or more substituted or unsubstituted epsilon caprolactam precursors.

17. A reaction mixture comprising one or more substituted or unsubstituted epsilon caprolactams in which said reaction mixture is prepared by a process which comprises: (a) subjecting one or more substituted or unsubstituted 6-hydroxyaldehydes to oxidation, optionally in the presence of an oxidation catalyst or an oxidation catalyst and promoter, to produce one or more substituted or unsubstituted 6-hydroxyacids and/or one or more substituted or unsubstituted epsilon caprolactam precursors, and (b) subjecting said one or more substituted or unsubstituted 6-hydroxyacids and/or said one or more substituted or unsubstituted epsilon caprolactam precursors to amination, optionally in the presence of an amination catalyst or an amination catalyst and promoter, and cyclization, optionally in the presence of a cyclization catalyst or a cyclization catalyst and promoter, to produce said reaction mixture comprising one or more substituted or unsubstituted epsilon caprolactams; wherein the amount of byproducts resulting from reduction and/or reductive amination of said one or more substituted or unsubstituted 6-hydroxyaldehydes is no greater than about 10 weight percent of the total of said one or more substituted or unsubstituted 6-hydroxyacids and/or one or more substituted or unsubstituted epsilon caprolactam precursors.

18. The reaction mixture of claim 16 in which the process further comprises subjecting said one or more substituted or unsubstituted epsilon caprolactam precursors comprising aminoamides to deamination, optionally in the presence of a deamination catalyst or a deamination catalyst and promoter, and cyclization, optionally in the presence of a cyclization catalyst or a cyclization catalyst and promoter, to produce said one or more substituted or unsubstituted epsilon caprolactams.

19. The reaction mixture of claim 17 in which the process further comprises derivatizing the one or more substituted or unsubstituted epsilon caprolactams, in which the derivatizing reaction comprises hydrogenation, esterification, polymerization, copolymerization, amination, alkylation, dehydrogenation, reduction, acylation, condensation, oxidation, silylation, and permissible combinations thereof.

* * * * *